(12) United States Patent
Masters et al.

(10) Patent No.: US 8,475,715 B2
(45) Date of Patent: Jul. 2, 2013

(54) RESONANT SENSOR SYSTEMS AND METHODS WITH REDUCED GAS INTERFERENCE

(75) Inventors: Brett P. Masters, Watertown, MA (US); Michael F. Miller, Hollis, NH (US)

(73) Assignee: BioScale, Inc., Cambridge, MA (US)

( * ) Notice: Subject to any disclaimer, the term of this patent is extended or adjusted under 35 U.S.C. 154(b) by 1266 days.

(21) Appl. No.: 11/502,168

(22) Filed: Aug. 10, 2006

(65) Prior Publication Data
US 2007/0059212 A1    Mar. 15, 2007

Related U.S. Application Data

(60) Provisional application No. 60/707,717, filed on Aug. 12, 2005.

(51) Int. Cl.
*G01N 27/00* (2006.01)

(52) U.S. Cl.
USPC ............ 422/82; 73/1.02; 73/19.03; 73/23.41; 73/23.42; 73/24.01; 422/68.1; 422/81; 422/82.04

(58) Field of Classification Search
USPC ............. 73/1.02, 19.03, 23.41–23.42, 24.01; 422/68.1, 82, 82.04
See application file for complete search history.

(56) References Cited

U.S. PATENT DOCUMENTS

| | | | |
|---|---|---|---|
| 4,789,804 A | 12/1988 | Karube et al. | 310/311 |
| 4,859,864 A | 8/1989 | Smith | 250/577 |
| 4,958,295 A * | 9/1990 | Davidson et al. | 702/25 |
| 5,023,053 A | 6/1991 | Finlan | 422/82.05 |
| 5,216,312 A | 6/1993 | Baer et al. | 310/313 D |
| 5,334,303 A | 8/1994 | Muramatsu et al. | 204/412 |
| 5,639,423 A | 6/1997 | Northrup et al. | 122/50 |
| 6,168,948 B1 | 1/2001 | Anderson et al. | 435/287.2 |
| 6,196,059 B1 | 3/2001 | Kosslinger et al. | 73/61.49 |
| 6,289,286 B1 * | 9/2001 | Andersson et al. | 702/19 |
| 6,321,588 B1 * | 11/2001 | Bowers et al. | 73/24.01 |
| 6,331,909 B1 | 12/2001 | Dunfield | 359/199 |
| 6,494,694 B2 | 12/2002 | Lawless et al. | 417/479 |
| 6,602,327 B2 | 8/2003 | Morse et al. | 95/261 |
| 6,629,449 B1 | 10/2003 | Kline-Schoder et al. | 73/19.03 |
| 6,653,124 B1 | 11/2003 | Freeman | 435/297.1 |
| 6,670,115 B1 | 12/2003 | Zhang | 435/5 |
| 6,848,625 B2 | 2/2005 | Takekuma et al. | 239/1 |
| 6,875,619 B2 | 4/2005 | Blackburn | 436/514 |
| 6,901,963 B2 | 6/2005 | Kim et al. | 137/833 |

(Continued)

OTHER PUBLICATIONS

Clark et al., Novel resonant-frequency sensor to detect the kinetics of protein adsorption, Dec. 2002, American Institute of Physics, Review of Scientific Instruments vol. 73, No. 12, p. 4339-4346.*

(Continued)

*Primary Examiner* — In Suk Bullock
*Assistant Examiner* — Robert Eom
(74) *Attorney, Agent, or Firm* — Proskauer Rose LLP

(57) ABSTRACT

A system having reduced gas interference that includes a fluid chamber and a resonant sensor device in fluid communication with a fluid in the fluid chamber. The system includes a fluid control device adapted to change at least one of the fluid flow or pressure within the fluid chamber to achieve substantial wetting of surfaces in proximity to the resonant sensor device. Fluid surfaces of the system can include a material to increase the wettability (e.g., hydrophilicity) of the fluid surfaces.

25 Claims, 4 Drawing Sheets

U.S. PATENT DOCUMENTS

| | | | |
|---|---|---|---|
| 6,939,451 B2 | 9/2005 | Zhao et al. | 204/451 |
| 6,949,176 B2 | 9/2005 | Vacca et al. | 204/547 |
| 7,014,966 B2 | 3/2006 | Pawloski et al. | 430/30 |
| 7,410,811 B2 | 8/2008 | Lin et al. | 436/526 |
| 2002/0009015 A1 | 1/2002 | Laugharn, Jr. et al. | 366/108 |
| 2003/0012693 A1 | 1/2003 | Otillar et al. | 422/58 |
| 2005/0043900 A1 | 2/2005 | Franda et al. | 702/25 |

OTHER PUBLICATIONS

Offer Letter for Sale of the BioScale B300 Instrument System Sent to a Customer on Sep. 9, 2004 (1 pg.).

Dubé et al., "A Si-Based FPW Sensor Array System with Polymer Microfluidics Integrated on a PCB", 2002 *IEEE*, pp. 460-465.

Li, Jishan et al., "Piezoelectric Immunosensor Based on Magnetic Nanoparticles with Simple Immobilization Procedures", Elsevier Science, Analytica Chimica Acta, vol. 481, (2003), pp. 191-198.

Christiansen, "Electronics Engineers' Handbook," 4$^{th}$ Ed., 1997, McGraw-Hill, Cover, Table of Contents and pp. 18.57-18.66.

Golio, "The RF and Microwave Handbook," CRC Press, 2001.

Plückthun, "Antibodies from *Escherichia coli*," Nature, vol. 347, Oct. 4, 1990, 347:497-498.

W. D. Huse et al., "Generation of a Large Combinatorial Library of the Immunoglobulin Repertoire in Phase Lambda," Science, vol. 246, (Dec. 8, 1989), pp. 1275-1281.

V. K. Chaudhary et al., "A rapid method of cloning functional variable-region antibody genes in *Escherichia coli* as single-chain immunotoxins," Proc. Natl. Acad. Sci., vol. 87 (Feb. 1990), pp. 1066-1070.

R. L. Mullinax et al., "Identification of human antibody fragment clones specific for tetanus toxoid in a bacteriophage λ immunoexpression library," Proc. Natl. Acad. Sci., vol. 87 (Oct. 1990), pp. 8095-8099.

J. Berg et al., "Bispecific antibodies that mediate killing of cells infected with human immunodeficiency virus of any strain," Proc. Natl. Acad. Sci., vol. 88 (Jun. 1991), pp. 4723-4727.

C. R. Wood et al., "High Level Synthesis of Immunoglobulins in Chinese Hamster Ovary Cells," The Journal of Immunology, vol. 145 (Nov. 1, 1990), pp. 3011-3016.

R. A. McGill et al., "Choosing polymer coatings for chemical sensors," Chemtech (Sep. 1994), pp. 27-37.

E. J. Houser et al., "Rational materials design of sorbent coatings for explosives: applications with chemical sensors," Talanta, vol. 54, 2001, pp. 469-485.

E. L. Lyle et al., "Acoustic coupling of transverse waves as a mechanism for the label-free detection of protein-small molecule interactions," Analyst 2002, No. 127, pp. 1596-1600.

L. Jiang et al., "Transient and sub-atmospheric performance of a closed-loop electroosmotic microchannel cooling system." Thermal Challenges in Next Generation Electronic Systems, Joshi & Garimella (eds) 2002, Millipress, Rotterdam, pp. 133-139.

J. C. Pyun et al., "Development of a biosensor for *E. coli* based on a flexural plate wave (FPW) transducer," Biosensors & Bioelectronics, vol. 13, 1998, pp. 839-845.

S. E. Cowan et al., "Ultrasonic Flexural-Plate-Wave Sensor for Detecting the Concentration of Settling *E. coli* W3110 Cells," Analytical Chemistry, vol. 71, No. 16, Aug. 15, 1999, pp. 3622-3625.

F. Josse et al., "Guided Shear Horizontal Surface Acoustic Wave Sensors for Chemical and Biochemical Detection in Liquids," Analytical Chemistry, Dec. 15, 2001, vol. 73, No. 24, pp. 5937-5944.

\* cited by examiner

RESONANT SENSOR SYSTEMS AND METHODS WITH REDUCED GAS INTERFERENCE

FIELD OF THE INVENTION

The invention relates to chemical and biological analyte sensing systems. More specifically, the invention relates to resonant sensor systems for measuring or detecting the physical characteristics of fluids or analytes in a fluid sample, and the reduction of gas interference in such systems.

BACKGROUND OF THE INVENTION

Resonant sensor systems are microelectromechanical systems ("MEMS") that can be used to measure the physical characteristics of a substance by detecting changes in resonant frequencies. Typically, resonant sensors utilize the ability of membranes to undergo physical deformation in response to external forces which cause vibrations or rhythmic motion. The membrane deformations are characterized by frequencies that are altered by the fluid medium surrounding the membrane, or by substances binding to the membrane that change the membrane's mass. By detecting frequencies in particular media or under particular conditions, resonant sensors are capable of generating signals that correspond to media or conditions (e.g., number or type of molecules in a solution) encountered by the resonant sensor.

In general, resonant sensor devices are capable of highly sensitive detection of changes in the physical characteristics of a fluid in contact with the sensor. However, resonant sensors are also highly sensitive to the presence of gas in a fluid, even if the gas is located relatively distant from the resonant surface of the resonant sensor device, because gases are compressible and, therefore, reduce the bulk fluid resistance to oscillations of the sensor surface. In most instances, gas is present in a sample or control fluid, or is trapped in areas of a fluid chamber where incomplete wetting of the surface occurs when fluid is introduced to the fluid chamber. Gas also can be formed in a sensor system as a vapor produced from heating a fluid, or by reducing the pressure of a fluid sample until the fluid transitions from a fluid state to a gas state. Furthermore, gas can nucleate to form bubbles or microbubbles (i.e., dimensions $\leq 400$ μm) anywhere in the system, including locations upstream of the fluid chamber (e.g., sample or control fluid reservoirs, inlet connectors, inlet valves, and inlet ports) or on surfaces within the fluid chamber, including the surface of the resonant sensor device.

Bubbles or undissolved gas present significant limitations on the detection sensitivity achieved with resonant sensor devices. For example, stable measurements have not been maintained for periods of time longer than a few minutes due to gas in resonant sensor systems (see, e.g., Pyun et al., (1998) *Biosensors & Bioelec.* 13: 839-845). The short durations of time provided by previous techniques did not allow for significant data to be obtained during an experiment. Moreover, signals were stable over frequency ranges of between fifty and several hundred Hz/MHz (see, e.g., Cowan et al., (1999) *Anal. Chem.* 71:3622-3626). Such detection instability has prevented the identification of small or moderate changes in the characteristics of a solution. Furthermore, small or medium-sized molecules in a fluid could not be detected but, rather, only the largest biomolecules could be detected by these systems.

A need therefore exists for systems and methods that reduce the effect of gas on the performance of resonant sensor systems.

SUMMARY OF THE INVENTION

The present invention depends, in part, on the discovery that gas interference is a significant problem in resonant sensor systems, and that gas interference can be reduced by causing variations in fluid flow rate and/or pressure which dislodge bubbles within the system or reduce pockets of gas at unwetted surfaces. In addition, the present invention depends, in part, upon the discovery that the use of wettable (e.g., hydrophilic) interior surfaces, including surfaces other than the resonant surfaces of resonant sensor devices, can reduce the presence of gas in a resonant sensor system and, thereby, reduce gas interference. Accordingly, the invention provides resonant sensor systems in which fluid is flowed through a fluid chamber with fluctuations in fluid flow rate and/or pressure, and/or in which the fluid chamber includes wettable (e.g., hydrophilic) interior surfaces, in order to reduce gas interference and improve performance.

The invention, in one aspect, features a resonant sensor system having reduced gas interference. The system includes a fluid chamber and a resonant sensor device in fluid communication with a fluid in the fluid chamber. The system also includes at least one inlet port and at least one outlet port in fluid communication with the fluid chamber. The system also includes a monitoring device to monitor at least one signal output by the resonant sensor device. The system optionally includes a fluid control device adapted to change at least one of the fluid flow or pressure within the fluid chamber to achieve substantial wetting of surfaces in proximity to the resonant sensor device. In certain embodiments, the fluid control device is adapted to change at least one of the fluid flow or pressure based on the signal output by the resonant sensor device.

In some embodiments, the system includes a pump to cause fluid to flow through the fluid chamber. Moreover, in some embodiments, the system includes an inlet valve adapted to selectively allow fluid flow through the inlet port. In certain embodiments, the fluid control device closes the inlet valve based on the signal output to produce at least one of transient fluid flows or pressure changes within the fluid chamber. Further, in some embodiments, the system includes a source of vibration to change fluid flow or pressure within the fluid chamber. In some embodiments, the dimensions of the fluid chamber are between about 10 μm and about 3 mm. In certain embodiments, at least one surface of the resonant sensor device forms an interior surface of the fluid chamber.

In certain embodiments, the resonant sensor device is a resonant membrane device. In other embodiments, the resonant sensor device is a flexural plate wave device. In certain embodiments, the flexural plate wave device can include at least one actuator and at least one sensor. In some of these embodiments, the actuator and sensor are associated with a plurality of interdigitated electrodes.

In another aspect, the invention provides a resonant sensor system having reduced gas interference, which includes a fluid chamber and a resonant sensor device in fluid communication with a fluid in the fluid chamber, at least one inlet means and at least one outlet means in fluid communication with the fluid chamber, and means for monitoring at least one signal output by the resonant sensor device and a means for changing at least one of the fluid flow or pressure within the fluid chamber based on the resonant signal output by the resonant sensor device.

In another aspect, the invention provides a resonant sensor system having reduced gas interference, which includes a fluid chamber defined by a plurality of interior surfaces, a resonant sensor device that defines at least one interior surface of the fluid chamber or disposed within the fluid chamber, and at least one inlet port and at least one outlet port in fluid communication with the fluid chamber. The system also includes an inlet valve adapted to allow fluid flow into the fluid chamber through the inlet port when the inlet valve is in an open position, and to prevent fluid flow into the fluid chamber through the inlet port when the inlet valve is in a closed position. The system also includes a first pump adapted to pump fluid from the fluid chamber through the outlet port. The system also includes electronic monitoring means for detecting a signal from the resonant sensor. Transiently closing the inlet valve with the first pump operating causes transient flows and pressures within the fluid chamber.

In certain embodiments, the system includes a first inlet reservoir which is in fluid communication with the fluid chamber when the inlet valve is in the open position, and which is not in fluid communication with the fluid chamber when the inlet valve is in the closed position. In some embodiments, the system includes a first connector allowing fluid communication between the first inlet reservoir and the inlet port, wherein the inlet valve is disposed along a portion of the length of the first connector.

The invention, in another aspect, features a fluid measurement system having reduced gas interference. The system includes a fluid chamber and a sensor in fluid communication with a fluid in the fluid chamber. The system also includes at least one inlet port and at least one outlet port in fluid communication with the fluid chamber. The system also includes a monitoring device to monitor at least one signal output by the sensor and a fluid control device adapted to change at least one of the fluid flow or pressure within the fluid chamber to achieve substantial wetting of surfaces in proximity to the sensor.

In some embodiments, the system includes an inlet valve adapted to selectively allow fluid through the at least one inlet port and a pump in fluid communication with the fluid chamber, whereby transiently closing the inlet valve with the first pump operating causes transient flows and pressures within the fluid chamber.

In some embodiments of each of the foregoing aspects and embodiments of the invention, at least one interior surface of the fluid chamber or resonant sensor device can include a material to increase the wettability of that surface. In certain embodiments, the material used to increase wettability is a hydrophilic material, such as one or more of a surfactant, a polymeric hydrocarbon, or an amphipathic protein. In certain embodiments, the hydrophilic surface is characterized by a water contact angle of less than about 90°. The surfactant can be, for example, Tergitol, NP40, Triton X-100, Tween® 20, Tween® 40, Tween® 65, TWEEN® 80, Tween® 85, 3-3 [(3-Cholamidopropyl)dimethylammonio]-1-propane-sulfonate, 2,4,7,9-Tetramethyl-5-decyne-4,7-diol ethoxylate, MERPOL® OJ, MERPOL® SE, or MERPOL® SH. In other embodiments, the polymeric hydrocarbon can be, for example, polyethylene glycol, poly(ethylene glycol) methyl ether, ethylene glycol monosalicylate, di(ethylene-d8-glycol), di(ethylene glycol) 2-ethylhexyl ether, di(ethylene glycol) benzyl ether, di(ethylene glycol-d2), or di(ethylene glycol) hexyl ether. In still other embodiments, the amphipathic protein can be albumin, ovalbumin, serum albumin, oleosins, gelatin, or casein. In further embodiments, the hydrophilic material can be, for example, polypropylene, polystyrene, doped polystyrene, polycarbonate, PTFE, ULTEM® or PET.

In some embodiments of each of the foregoing aspects and embodiments, the resonant sensor device includes a resonant surface bearing a plurality of capture agents capable of binding an analyte. In certain embodiments, the capture agents can be antibodies, Fab fragments, and single chain variable region antibody fragments (scFvs). In some embodiments, the resonant surface can include a material selected from the group consisting of gold, silicon dioxide, gallium arsenide, polypropylene, polystyrene, doped polystyrene, polycarbonate, PTFE, ULTEM® and PET. In some embodiments, the capture agents can be disposed on the resonant surface by linkages to organic chains associated with the resonant surface. In specific embodiments, the organic chains can be thiol-terminated alkyl and carboxyl-terminated alkyl chains. In other embodiments, the organic chains can be covalently linked to a hydrophilic material selected from the group consisting of surfactants, polymeric hydrocarbons, and amphipathic proteins, as described above.

The invention, in another aspect, features a method of reducing interference from gas in a resonant sensor system. The method involves monitoring at least one signal output by a resonant sensor device that is in fluid communication with a fluid chamber having at least one inlet port and at least one outlet port. The method also involves changing at least one of the fluid flow or pressure within the fluid chamber to achieve substantial wetting of surfaces in proximity to the resonant device.

In some embodiments, the fluid flow or pressure is changed based on at least one signal output by the resonant sensor device. The signal can indicate the presence of gas in the fluid. In some embodiments, the method also involves pumping the fluid through the fluid chamber. In other embodiments, the method involves varying a state of an inlet valve to alter fluid flow through the inlet port to change fluid flow or pressure within the fluid chamber. In other embodiments, transiently varying a state of the inlet valve as fluid is pumped through the fluid chamber to change fluid flow or pressure within the fluid chamber can reduce interference associated with the gas. In some embodiments, the method also involves transiently varying a state of the inlet valve repeatedly to change fluid flow or pressure and monitoring at least one signal output by a sensor in fluid communication with the fluid chamber until reduction of gas interference is indicated. In particular embodiments, the sensor is the resonant sensor device. In other particular embodiments, the method involves varying the state of the inlet valve between an open position and a closed position in less than about 1 second, or less than about 0.5 second.

In certain embodiments, the step of monitoring involves monitoring a resonant frequency associated with the resonant device during a time period of consistent fluid flow. In other embodiments, the method also involves changing the fluid flow or pressure within the fluid chamber based on whether a value associated with the resonant frequency varies by more than a pre-determined amount. In particular embodiments, the pre-determined amount is between about $5 \times 10^{-1}$ parts and about $1 \times 10^4$ parts.

In certain embodiments, the method involves varying a state of an outlet valve to alter fluid flow out of the outlet port to change the fluid flow or pressure within the fluid chamber. In some embodiments, the method involves varying fluid flow during the step of monitoring.

In some embodiments, a surfactant is introduced into the fluid chamber prior to flowing a sample fluid through the fluid chamber. In some embodiments, the surfactant can be Tergitol, NP40, Triton X-100, Tween® 20, Tween® 40, Tween® 65, TWEEN® 80, Tween® 85, 3-[(3-Cholamidopropyl)dimethylammonio]-1-propanesulfonate, 2,4,7,9-Tetramethyl-5-decyne-4,7-diol ethoxylate, MERPOL® OJ, MERPOL® SE, or MERPOL® SH. In further embodiments, the method involves introducing a material) to increase the wettability of at least one surface of the fluid chamber. In particular embodiments, the material is a hydrophilic material, as described above.

The invention, in another aspect, features a method of reducing interference from gas in a fluid chamber, by monitoring at least one signal output by a sensor that is in fluid communication with a fluid chamber having at least one inlet port and at least one outlet port, and changing at least one of the fluid flow or pressure within the fluid chamber to achieve substantial wetting of surfaces in proximity to the resonant device.

In certain embodiments, the fluid flow or pressure is changed based on the at least one sensor signal output by the sensor. In some embodiments, the sensor signal indicates the presence of gas in the fluid. In some embodiments, the method also involves pumping the fluid through the fluid chamber. In some other embodiments, the method involves varying a state of an inlet valve to alter fluid flow through the inlet port to change fluid flow or pressure within the fluid chamber. In yet other embodiments, the method involves transiently varying a state of the inlet valve as fluid is pumped through the fluid chamber to change fluid flow or pressure within the fluid chamber to reduce interference from gas in the fluid. In additional embodiments, the method involves transiently varying a state of the inlet valve repeatedly and monitoring the signal output by the sensor until a resonance associated with the signal returns to a predetermined resonance value.

The invention, in another aspect, provides a method of reducing interference from gas in a resonant sensor system, by providing a resonant sensor system which includes a fluid chamber defined by a plurality of interior surfaces and a resonant sensor device defining at least one interior surface of the fluid chamber or disposed within the fluid chamber, at least one inlet port and at least one outlet port in fluid communication with the fluid chamber, an inlet valve to selectively allow fluid flow through the inlet port and a pump to pump fluid through the fluid chamber, and transiently operating the inlet valve with the pump operating to produce transient flows and reductions of pressure within the fluid chamber thereby reducing interference from gas in the fluid.

In certain embodiments, the valve is moved between a closed and an open position in less than about 1 second, or in less than about 0.5 seconds. In some embodiments, the method involves flowing a surfactant fluid through the fluid chamber to increase the wettability of the interior surfaces prior to flowing a sample fluid through the fluid chamber.

The invention, in another aspect, provides a method of reducing interference from gas in a resonant sensor system, by providing a resonant sensor system that includes a fluid chamber defined by a plurality of interior surfaces and a resonant sensor device defining at least one interior surface of the fluid chamber or disposed within the fluid chamber, at least one inlet port and at least one outlet port in fluid communication with the fluid chamber, an inlet valve adapted to allow fluid flow into the fluid chamber through the inlet port when the inlet valve is in an open position, and to prevent fluid flow into the fluid chamber through the inlet port when the inlet valve is in a closed position, a first pump adapted to pump fluid from the fluid chamber through the outlet port and electronic monitoring means for detecting a signal from the resonant sensor device, and monitoring the signal to detect the presence of gas in a fluid in the fluid chamber. The method also involves transiently operating the inlet valve with the pump operating to change the flow and pressure within the fluid chamber to reduce the interference associated with the gas in the fluid. The method can also involve repeating the steps of monitoring the signal and of transiently operating the inlet valve with the pump operating until gas is not detected.

In further embodiments, monitoring involves observing a frequency associated with the signal during a period of consistent flow of a uniform fluid sample through the fluid chamber, and detecting relative changes in the operating frequency greater than about $1-2\times10^{-6}$ parts during the period of consistent flow of the uniform fluid sample. In other embodiments, the period can be between about 1 and about 2 seconds. In certain other embodiments, the period can be less than about 1 second.

In some embodiments, the step of monitoring can involve determining a resonant frequency associated with the signal during a period of varied flow of a uniform fluid sample through the fluid chamber and detecting relative changes in resonant frequency greater than about $1-2\times10^{-6}$ parts during the period of varied flow of uniform fluid sample. In particular embodiments, the period can be between about 1 second and about 2 seconds. In further particular embodiments, the period can be less than about 1 second.

In some embodiments, the method also involves flowing a surfactant fluid through the fluid chamber to increase the wettability of the interior surfaces prior to flowing a sample fluid through the fluid chamber, as described above.

The invention, in another aspect, features a cartridge for a resonant device system having reduced gas interference. The cartridge includes a fluid chamber. The cartridge also includes a resonant device defining at least one interior surface of the fluid chamber, or disposed within the fluid chamber, in which the interior surface of the fluid chamber, or the surface of the resonant device, includes a wettable surface. The cartridge also includes at least one inlet port and at least one outlet port in fluid communication with the fluid chamber. In some embodiments, the wettable surface is a hydrophilic surface, as described above.

In certain embodiments, the cartridge includes an inlet valve adapted to allow fluid flow into the fluid chamber through the inlet port when the inlet valve is in an open position, and to prevent fluid flow into the fluid chamber through the inlet port when the inlet valve is in a closed position. In some embodiments, the cartridge includes an outlet valve adapted to allow fluid flow out of the fluid chamber when the outlet valve is in an open position, and to prevent fluid flow out of the fluid chamber when the outlet valve is in a closed position.

BRIEF DESCRIPTION OF THE DRAWINGS

The foregoing and other objects, feature and advantages of the invention, as well as the invention itself, will be more fully understood from the following illustrative description, when read together with the accompanying drawings which are not necessarily to scale.

DETAILED DESCRIPTION OF ILLUSTRATIVE EMBODIMENTS

Figure 1:
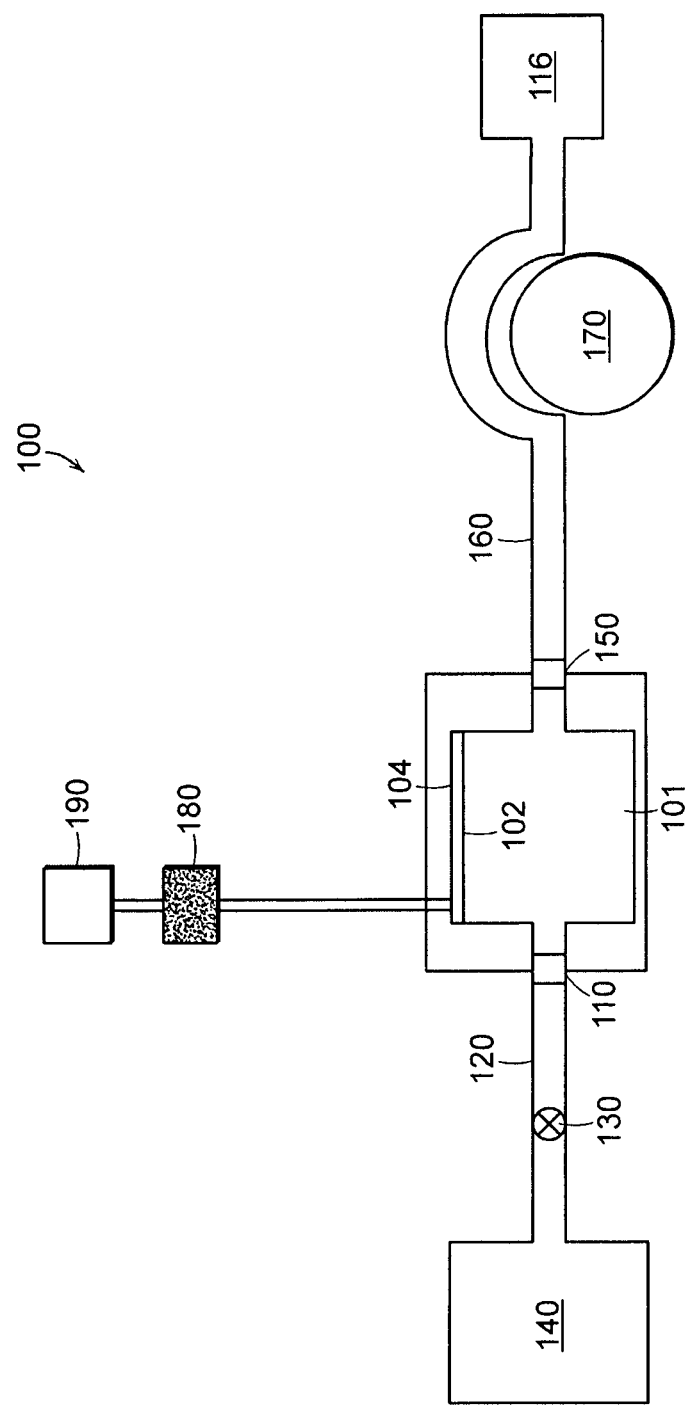
FIG. 1 is a partial schematic view of resonant sensor system of one embodiment of the invention.

The patent, technical and scientific publications referred to herein establish knowledge that was available to those of ordinary skill in the art at the time the invention was made. The entire disclosures of the issued U.S. patents, published and pending patent applications, and other references cited herein are hereby incorporated by reference.

DEFINITIONS

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent or later-developed techniques, which would be apparent to one of skill in the art. In addition, in order to more clearly and concisely describe the subject matter which is the invention, the following definitions are provided for certain terms which are used in the specification and appended claims.

As used herein, the term "resonant sensor" means a device that detects at least one analyte in a fluid by measuring the variation of the resonance characteristics of at least one surface of the device caused by the binding of an analyte to a capture agent on the surface. A resonant sensor device also detects changes in the bulk properties of a fluid (e.g., viscosity, density, and speed of sound in the fluid).

As used herein, the term "resonant movement" means repeated motion between first and second positions over time. Resonant movement can vary in frequency and/or amplitude over time. The frequency of resonant movement is referred to as the resonant frequency.

As used herein, the term "fluid chamber" means an at least partially enclosed space in which a resonant sensor surface is disposed such that a resonant frequency can be detected for the resonant sensor surface for a given fluid sample. In certain embodiments, the resonant sensor surface has capture agents disposed thereon for detection of analytes. In other embodiments, the resonant sensor surface disposed within the fluid chamber need not have capture agents.

As used herein, the term "resonant surface" means that surface of a resonant sensor device which undergoes resonant movement or can undergo resonant movement.

As used herein, the term "analyte" means a molecule or compound in a fluid sample that is being measured or detected, or is intended to be measured or detected, by a resonant sensor device.

As used herein, the term "capture agent" means a molecule or compound that can bind with an analyte in a fluid by molecular interactions (e.g., by one or more of covalent bonding, ionic bonding, hydrogen bonding, London forces, or van der Waals forces) sufficient to maintain an association between the capture agent and the analyte.

As used herein, the term "baseline frequency" means a resonant frequency of a resonant sensor device that has been determined empirically, theoretically, or extrinsically for a given fluid (in the presence or absence of an analyte). The baseline frequency is used, for example, for comparison to a frequency measured by the resonant sensor system after the introduction of a sample fluid within a fluid chamber, or for comparison to a frequency measured by the resonant sensor system after performing a method to reduce gas interference. The baseline frequency can be determined for a fluid with or without an analyte to be measured (e.g., a sample fluid, a control fluid or wetting fluid).

As used herein, the term "gas" means any molecules that exist in a vapor or gaseous state, undissolved in a fluid. Gas can be associated with interior surfaces within a fluid chamber of a resonant sensor system, or can be in the form of bubbles in a fluid within the fluid chamber. Further, gas can exist in other locations of the resonant sensor system (e.g., inlets, conduits, tubes, passages, and reservoirs).

As used herein, the term "interference" means any deleterious influence on the ability of a resonant sensor system to measure a resonant frequency for a particular fluid. For example, interference includes fluctuations in the frequency detected by a resonant sensor system that are not caused by the presence or concentration of an analyte in a fluid or by commanded or known variation of control parameters (e.g., fluid pressure, flow rate, or fluid composition).

As used herein, the term "wettable" means capable of associating with a fluid. With respect to a surface, the term "wettable" means characterized by a fluid contact angle of greater than 90° which encourages wetting of the surface such that the fluid spreads on the surface.

As used herein, the term "hydrophilic" means capable of associating with an aqueous solution by forming hydrogen bonds with water or other hydrophilic molecules in the solution. With respect to a surface, the term "hydrophilic" means characterized by a water contact angle of greater than 90°, which encourages wetting of the surface.

As used herein, the term "surfactant" means a surface-active molecule that reduces the surface tension of a fluid at an interface with a gas or solid surface. As used herein, the term "surface-active" means associating with a surface or interface through means such as covalent bonding, hydrogen bonding, van der Waals forces, London forces, or ionic bonding.

As used herein, "amphipathic protein" means a protein that contains at least one hydrophilic domain and at least one hydrophobic domain.

As used herein, the term "organic chain" means any molecular moiety that consists of at least two atoms selected from carbon, nitrogen, oxygen, sulfur and phosphorus. An organic chain can also include other atoms, including halogens and metals. An organic chain can be linear or branched, or can contain ring structures. In addition, an organic chain can include only single bonds, or can include one or more double bonds or triple bonds.

As used herein, the term "polymeric hydrocarbon" means a molecule that contains covalently bound repeating units of a hydrocarbon moiety. The hydrocarbon moiety consists of at least two carbon atoms in which at least one carbon atom is bonded to at least one hydrogen atom. In addition, polymeric hydrocarbons can include ether, alcohol, glycol, ester, carboxyl, carbonyl, amide, amine, or other functional groups useful for association with an aqueous environment or as reactive groups for covalent bonding to organic chains or capture agents.

As used herein, the term "viscous boundary layer" means a region in which viscous effects reside between a solid surface and an inviscid free-stream of fluid.

As used herein, the recitation of a numerical range for a variable is intended to convey that the invention may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values $\geq 0$ and $\leq 2$ if the variable is inherently continuous.

As used herein, the term "reduced" means decreased by at least 5% from a reference value.

As used herein, the term "increased" means increased by at least 5% from a reference value.

As used herein, unless specifically indicated otherwise, the word "or" is used in the inclusive sense of "and/or" and not the exclusive sense of "either/or."

Resonant Sensor Systems.

The present invention depends, in part, on the discovery that gas interference is a significant problem in resonant sensor systems, and that gas interference can be reduced by causing variations in fluid flow rate or pressure which dislodge bubbles within the system or reduce pockets of gas at unwetted surfaces. In addition, the present invention depends, in part, upon the discovery that the use of wettable (e.g., hydrophilic) interior surfaces, including surfaces substantially removed from a resonant surface, can reduce the presence o gas in a resonant sensor system and, thereby, reduce gas interference. Accordingly, the invention provides resonant sensor systems in which fluid is flowed through a fluid chamber with fluctuations in flow rate or pressure, and/or in which the fluid chamber includes wettable (e.g., hydrophilic) interior surfaces, in order to reduce gas interference and improve performance.

Resonant sensors are devices that are used to measure and/or detect an analyte in a fluid sample or to measure the properties of a fluid (e.g., viscosity, density, and speed of sound in the fluid). In one embodiment, a resonant sensor device is used to measure the amount of analyte in a fluid sample by measuring the change in the resonant frequency of a resonant surface caused by the binding of the analyte to capture agents on the resonant surface. In this case, the resonant sensor has at least one resonant surface to which at least one capture agent is bound, and the capture agent is capable of selectively binding at least one analyte, which may be present within the fluid sample. The resonant sensor device also includes a means for inducing resonant movement of the resonant surface to which the capture agents are bound, and electronic monitoring means for detecting a signal corresponding to the resonant frequency. In operation, the binding of analytes to the capture agents changes the effective mass of the resonant surface and thereby alters the resonant frequency, which is detected by the electronic monitoring means. The change in resonance of the resonant surface depends strongly on the presence of gases/bubbles in proximity to the resonant surface, as well as in locations relatively distant from the resonant surface.

In other embodiments, resonant sensor devices are used to determine properties of the fluid (e.g., viscosity, density, and speed of sound in the fluid) flowing through the fluid chamber of the resonant sensor system. In such embodiments, the resonant sensor device can have capture agents attached to its surface or it can be designed without capture agents attached to the surface. Fluid, with or without analyte, is allowed to enter the fluid chamber, thereby contacting the resonant surface. As fluid contacts the resonant surface, a fluid communication layer is established near the resonant surface. Within the fluid communication layer, viscous coupling of the fluid to the resonant surface serves to mass load and increase the dissipation of the resonating sensor surface. A change in the viscous coupling (i.e., viscosity or density change) is determined based on the corresponding change in resonant frequency of the resonant surface. The change in resonant frequency of the resonant surface depends strongly on the presence of gases/bubbles in proximity to the resonant surface, as well as in locations relatively distant from the resonant surface.

In addition, the resonant sensor device can be used to measure the speed of sound in a fluid sample. Resonant sensor devices measuring the speed of sound in a fluid sample generate a coupled acoustic response in the fluid communication layer covering the surface. An acoustic skin depth results when the device motion generates bulk compression of the fluid. Coupled resonance is established between the fluid and the resonant surface. The coupled acoustic response of the device (device plus liquid) depends strongly on the presence of gases/bubbles in proximity to the resonant surface, as well as in locations relatively distant from the resonant surface.

FIG. 1 is a partial schematic view of a resonant sensor system 100 constructed according to one embodiment of the invention. The resonant sensor system 100 includes a fluid chamber 101, which is in fluid communication with an inlet port 110 and an outlet port 150. The inlet port 110 is in fluid communication with an inlet connector 120 that allows fluid to flow into the fluid chamber 101 from an optional reservoir 140. An inlet valve 130 located along inlet connector 120 can be brought into a first closed position to prevent fluid flow through the inlet connector 120 and inlet port 110 into the fluid chamber 101. The inlet valve 130 can be moved to a second open position that allows fluid flow through the inlet connector 120 and inlet port 110, thereby allowing fluid flow into the fluid chamber 101. The outlet port 150 is in fluid communication with an outlet connector 160 that allows fluid to flow out of the fluid chamber 101.

The resonant sensor system 100 also includes a fluid control device 170 (e.g., a pump) disposed along the outlet connector 160 (as shown) or at the outlet port 150 (not shown) for pumping a fluid sample through the fluid chamber 101. The resonant sensor system 100 also includes an optional reservoir 116 connected to the outlet connector 160. Fluid flowing out of the fluid chamber 101 and through the outlet connector 160 passes into the reservoir 116.

In this embodiment, the fluid chamber 101 includes a resonant sensor device 104 that has a resonant surface 102 that forms an interior surface or wall of the fluid chamber 101. Alternatively, the resonant surface 102 may, instead, be disposed within the interior of the fluid chamber 101. The resonant surface 102 is in fluid communication with fluid that flows through the fluid chamber 101. In some embodiments, internal dimensions of the fluid chamber 101 are between about 10 µm and about 3 mm. The specific dimensions of the fluid chamber 101 can be determined by convenience or by the requirements of a specific application, such as the volume of fluid that is to be flowed through the fluid chamber 101.

The resonant surface is operably connected to an electronic monitoring device 180 that is capable of measuring various signals associated with the operation of the resonant sensor system 100. In this embodiment, the electronic monitoring device 180 is capable of measuring signals corresponding to the resonant frequency of the resonant surface 102. The electronic monitoring means 180 is in electrical connection with a data display, storage and/or analysis device 190. The electrical detection of resonant frequency can be implemented through a variety of means including, but not limited to, phase tracking and period and frequency counting (see, e.g., Christiansen, *Electronics Engineers Handbook*, 4th Ed. McGraw Hill; Golio, *The RF and Microwave Handbook*, CRC Press).

The electronic monitoring device 180 can measure signals from the resonant device during time periods when there is consistent fluid flow or pressure. Alternatively, the electronic monitoring device 180 can measure signals during time periods when there is varying fluid flow or pressure.

In some embodiments, the electronic monitoring device 180 is also connected (directly or indirectly) to other components and devices of the resonant sensor system 100. The electronic monitoring device 180 can be capable of controlling the operation of, for example, the pump 170 or the inlet valve 130. In this manner, an operator or an automated controller located within the electronic monitoring device 180 can control fluid flow and pressure in the resonant sensor system 100 by altering, for example, the speed of the pump 170 and/or the state (e.g., open, closed, or partially open position) of the inlet valve 130. In some embodiments, operation of the pump 170 and or inlet valve 130 is controlled based on at least one signal output by the resonant sensor device 100.

In alternative embodiments, a separate sensor (not shown) may be used to monitor properties of the resonant sensor system 100 to aid with detecting the presence of gas within a fluid in the resonant sensor system 100 and with reducing the presence of gas within the system 100. By way of example, a pressure sensor sensitive to the presence of gas can be used to monitor pressure fluctuations attributable to the presence of gas in the fluid. In this manner, the electronic monitoring device 180 can be used to detect the presence of gas in, for example, the fluid chamber 101. The electronic monitoring device then can send a signal to the pump 170 and/or valve 130 as described below to reduce the presence of gas in the fluid chamber 101.

Figure 2:
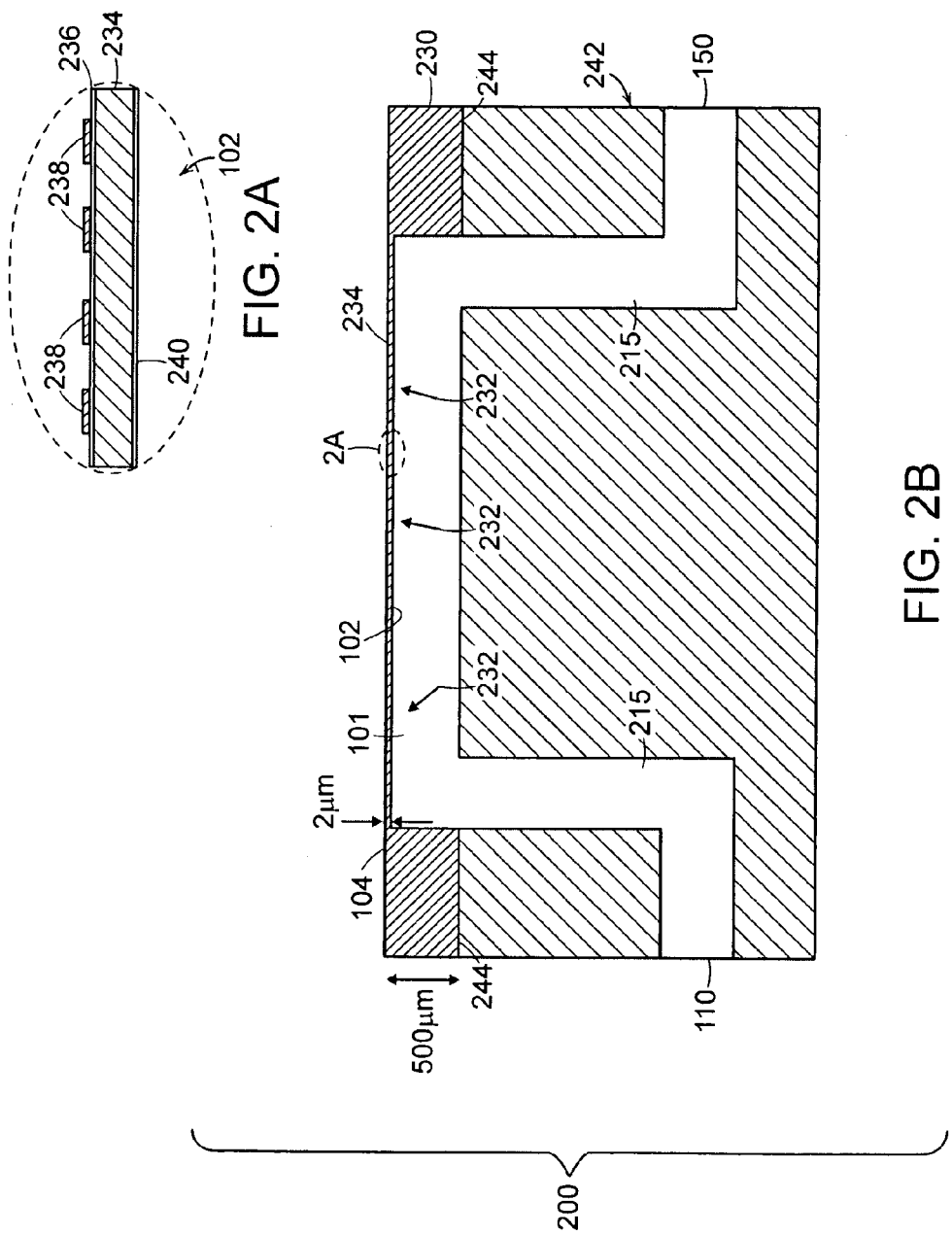
FIG. 2 is a partial schematic view of an exemplary resonant sensor device and fluid chamber of one embodiment of the invention.

FIG. 2 illustrates an embodiment in which a cartridge 200 is provided which includes the resonant sensor device 104, fluid chamber 101, inlet port 110 and an outlet port 150. In some embodiments, the cartridge 200 is a consumable unit which engages with a reusable unit that includes the remaining elements of the resonant sensor system 100, and the cartridge can be replaced by an operator if it becomes worn-out or fouled. In other embodiments, the cartridge 200 can be replaced by the operator in order to change the property of the sensor (e.g., change analytes detected). In one embodiment, the cartridge 200 and/or resonant sensor device 104 is rectangular in shape. The cartridge 200 and/or resonant sensor device 104 can, alternatively, be circular or elliptical, or some other planar shape. In some embodiments, the resonant sensor device 104 is a resonant membrane device where the resonant surface is a membrane-like structure. In other embodiments, the resonant sensor device 104 is a flexural plate wave device.

In certain embodiments, the resonant sensor device 104 is constructed from a silicon wafer 230, using micro-fabrication techniques known in the art. For example, in some embodiments, a cavity 232 is etched into the wafer 230 to produce a thin, suspended membrane 234. The depth of the cavity 232 is determined to be just slightly less than the wafer 230 thickness, in order to produce a thin membrane. In one specific example, the overall wafer 230 thickness can be approximately 500 µm, and the membrane can be approximately 1.6 mm long, 0.3 mm wide and 2 µm thick. The cartridge 200 includes a body 242 that defines one or more fluid passages 215 that direct fluid from the inlet port 110 to the cavity 232 and out through the outlet port 150. The fluid passages 115 and cavity 232 together define the fluid chamber 101. In some embodiments, the body 242 is part of a manifold that accommodates multiple resonant sensor devices 104 to enable one test to be performed on multiple fluids at the same time, or multiple tests to be performed on one fluid at the same time.

A very thin outer layer of material 236 (e.g., ~0.5 µm of a piezoelectric material such as aluminum nitride (AlN) or another suitable material known in the art) is deposited on the outer surface (i.e., the surface opposite the cavity 232) of the membrane 234, as shown in the expanded view inset of FIG. 2. Two sets of interdigitated metal electrodes 238 (one set functioning as an actuator or transmitter, and the other set as a sensor or receiver) are deposited upon the thin outer layer 236. Optionally, a thin inner layer 240 (e.g., ~500 Å of gold) is deposited on the inner surface (i.e., the surface facing the cavity 232) of the membrane 234 to facilitate immobilization of capture agents, as described in more detail below.

In a resonant sensor device 104, strain energy is carried in bending and tension in the device. In some embodiments, it is desirable for the thickness-to-wavelength ratio of the resonant sensor device 104 to be less than one, and in some cases much less than one. In general, the wavelength, $\lambda$, of the resonant sensor device 104 is approximately equal to the pitch of the interdigitated electrodes as described herein. For example, in one specific embodiment, the thickness-to-wavelength ratio of the resonant sensor device 104 can be approximately 2 µm/38 µm. In other embodiments, the resonant sensor device 104 is designed to isolate a particular mode (e.g., any mode from zero order mode to higher order modes) or bandwidth of modes associated with the device. For example, in the specific embodiment, a resonant sensor device 104 having a thickness/wavelength of 2 µm/38 µm as described above would isolate the $80^{th}$ mode of the resonant sensor device 104. The resonant sensor device 104 can be designed to achieve this effect by selecting a particular pattern for the interdigitated electrodes deposited on the device. The electrodes can be deposited onto a surface composed of an electroactive material, such as gold, aluminum or other suitable material. When fluid is in contact with the cavity 232 side of the membrane 234, the reference signal of the structure is, in the specific embodiment described above, between about 15 and about 25 MHz.

In operation, electronic monitoring device 180 (referring to FIG. 1) applies a time-varying electrical signal to at least one set of electrodes 238 to generate vibrations in the suspended membrane 234. The electronic monitoring device 180 also monitors the vibrational characteristics of the membrane 234 by receiving a sensor signal from at least a second set of electrodes 238. The electronic monitoring device 180 compares a reference or baseline signal to the sensor signal from the second set of electrodes to determine the changes in the relative magnitude and phase angle of the sensor signal as a function of frequency. The electronic monitoring device 180 interprets these changes to detect the presence of a targeted analyte in the fluid, or to determine other properties of the fluid. In some embodiments, the instrument/control electronics also determine, for example, the concentration of the targeted analyte on the inner surface of the membrane 234.

Operation of the pump 170 causes fluid to flow through the resonant sensor system 100. In the embodiment shown in FIG. 1, the pump 170 is located on the outlet side of the fluid chamber 101. The pump 170 may be, for example, a peristaltic pump. An exemplary peristaltic pump is an Instech P625/275 (Instech Laboratories, Inc. Plymouth Meeting, Pa.). Operation of the pump 170 with the inlet valve 130 in the open position induces fluid flow from the reservoir 140 through the inlet connector 120 through the inlet port 110 into the fluid chamber 101. The fluid interacts with the sensor surface 102 of the resonant sensor device 104 in the fluid chamber 101.

The fluid exits the fluid chamber 101 via the outlet port 150 and passes through the outlet connector 160 to be deposited in the optional reservoir 116 (e.g., a waste reservoir).

In some embodiments (not shown), the pump 170 is located on the inlet side of the fluid chamber 101. Similarly, the pump 170 operates to pump fluid through the resonant sensor system 100. In some embodiments, fluid flow through the resonant sensor system 100 is induced by gravity, allowing the fluid to flow passively out of the reservoir 140, through the inlet connector 120 and into the inlet port 110. The fluid then flows from the inlet port 110 into the fluid chamber 101, and then through the outlet port 150 and out of the outlet connector 160 to the optional reservoir 116.

It should be noted that there can be multiple inlet ports and inlet connectors, and/or multiple outlet ports and outlet connectors, without altering the overall functionality of the system 100. In those embodiments with multiple inlet ports and inlet connectors, there may be multiple inlet valves for controlling the source of fluid entering the fluid chamber 101. Alternatively, there can be multiple inlet connectors that lead to a single inlet port, with one or more inlet valves for controlling the source of fluid entering the fluid chamber 101. In those embodiments with multiple outlet ports and outlet connectors, there can be multiple pumps and optional outlet valves for controlling the flow of fluid exiting the fluid chamber 101. Alternatively, there can be multiple outlet connectors, which lead to a single outlet port, with one or more outlet valves for controlling the flow of fluid exiting the fluid chamber 101. Further, fluid control devices other than pumps also are contemplated for use in the systems and methods of the invention described herein to cause or assist with flowing fluid through the resonant sensor system.

Figure 3:
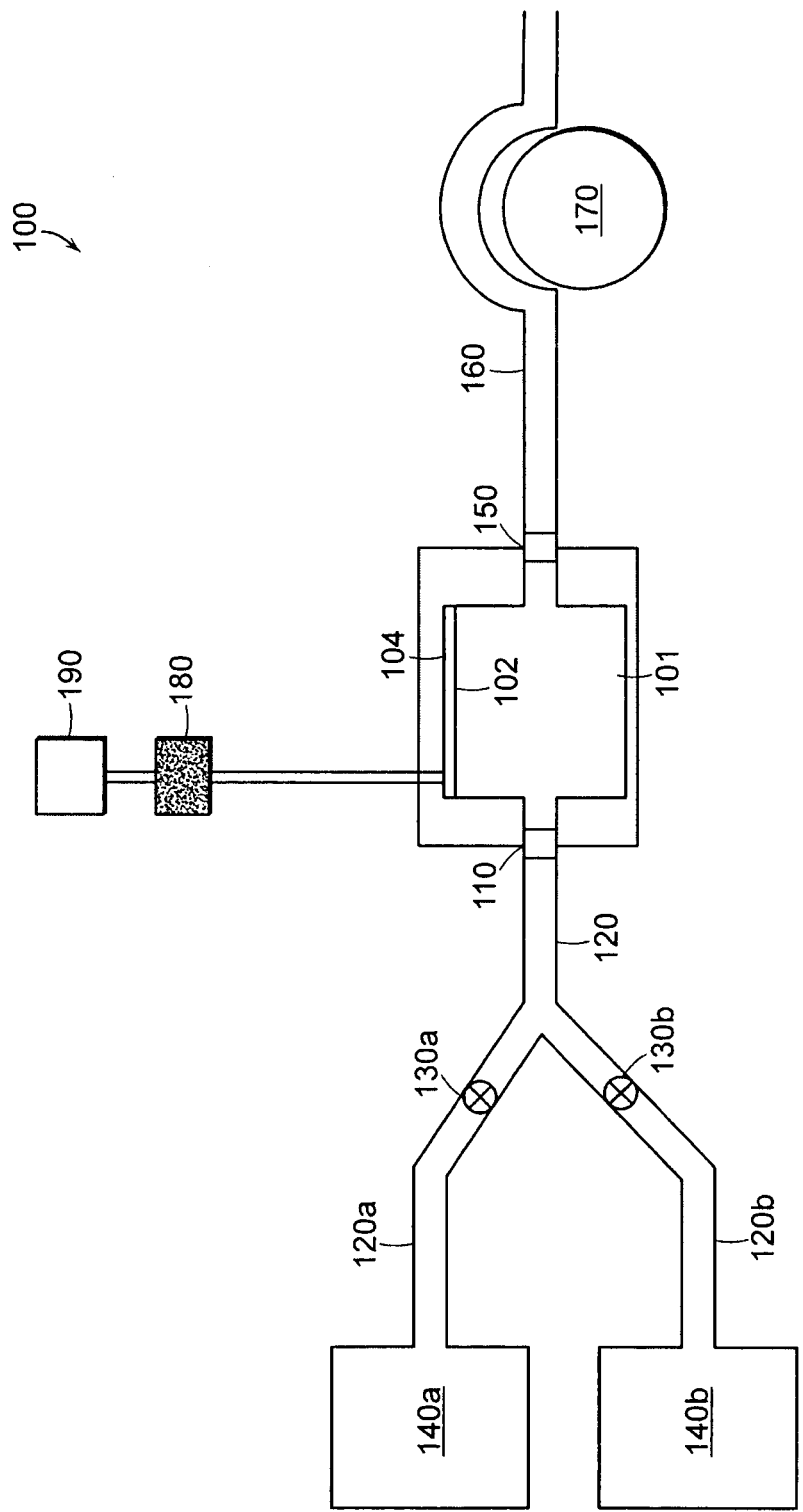
FIG. 3 is a partial schematic view of a resonant sensor system of one embodiment of the invention.

For example, FIG. 3 is a partial schematic view of a resonant sensor system 100 constructed according to another embodiment of the invention. The resonant sensor system 100 includes a fluid chamber 101 that is in fluid communication with an inlet port 110 and an outlet port 150. The inlet port 110 is in fluid communication with an inlet connector 120 that branches into two inlet connectors 120a and 120b. Fluid flows into the fluid chamber 101 from either of two reservoirs 140a and 140b that are connected to inlet connectors 120a and 120b, respectively. Reservoirs 140a and 140b can contain different sample fluids, or one can contain a sample fluid and the other can contain a control fluid (e.g., buffer fluid without analyte or a wetting solution).

Fluid flow from the reservoirs 140a and 140b is selectively controlled by respective inlet valves 130a and 130b located along inlet connectors 120a and 120b. By way of example, inlet valve 130a allows fluid to flow from the reservoir 140a through inlet connector 120a into inlet connector 120 when inlet valve 130a is placed in an open position. Alternatively, inlet valve 130a prevents fluid to flow from the reservoir 140a through inlet connector 120a into inlet connector 120 when inlet valve 130a is placed in an open position. A controlled amount of fluid can be allowed to flow from the reservoir 140a through inlet connector 120a, and into inlet connector 120 by partially opening the inlet valve 130a. Fluid flow out of reservoir 140b through inlet connector 120b and through inlet connector 120 can be achieved similarly by controlling the inlet valve 120b. If only one of inlet valves 130a and 130b is in the open position at any given time, fluid flow will occur from only one of reservoirs 140a and 140b through the inlet connector 120.

As described regarding FIG. 1, outlet port 150 of the resonant sensor system 100 of FIG. 3 is in fluid communication with an outlet connector 160. Pump 170 is disposed along the outlet connector 160 (as shown) or at the outlet port 150 (not shown) for pumping a fluid sample through the fluid chamber 101. The fluid chamber 101 includes a resonant surface 102, which is operably connected to an electronic monitoring device 180 that is capable of measuring the resonant frequency of the resonant surface 102 and transmitting the signal to a data display, storage and/or analysis device 190. Although FIG. 3 shows a system 100 with two reservoirs 140a and 140b, the resonant sensor systems of the invention can be produced with greater numbers of reservoirs and corresponding inlet connectors or inlet valves.

Reduction of Gas Interference by Varying Flow Rate and Pressure

Gas present in a fluid in a resonant sensor system interferes with the accurate measurement of, for example, the resonant frequency associated with the resonant surface. The interference is particularly severe when the gas is located within the fluid chamber of the resonant sensor device. Further, it is difficult to achieve good system performance (e.g., achieve repeatable, stable, or accurate measurements) when the amount or location of gas in the system changes over time. The interference is observed as either (1) fluctuating resonant frequencies in which the fluctuations are large relative to a baseline or average frequency, or (2) relatively constant resonant frequencies that differ from expected values by a relatively large amount. Alternatively, the presence of such gas can be assumed, and prophylactic measures can be taken to remove it.

Expected values for resonant frequencies can be derived empirically based on previous measurements made with a particular resonant sensor system in which the same or substantially similar sample fluids or control fluids are measured using the same or substantially similar resonant sensor devices. Alternatively, one of skill in the art can determine an expected frequency or acceptable fluctuations in resonant frequency by mathematical calculations based upon known properties of the resonant sensor device, the sample or control fluids, and the analytes. Expected values for common or intended sample or control fluids also can be determined from printed product instructions, scientific publications or other means. The skilled practitioner can also establish such expected values by routine experimentation.

Thus, regarding for example FIG. 1, to generate a baseline frequency empirically, fluid from the fluid reservoir 140 is flowed into the fluid chamber 101 by moving inlet valve 130 to the open position. The pump 170 is operated continuously to facilitate the flow of fluid out of the fluid reservoir 140. The fluid enters the fluid chamber 101 via the inlet port 110, making contact with the resonant surface 102 disposed within the fluid chamber 101. Electronic monitoring means 180 detects at least one signal provided by the resonant sensor device 104 and transmits the signal to data device 190. In the absence of gas interference, the resonant sensor device 104 exhibits a characteristic or baseline resonant frequency which is substantially constant and which is a function of the structural properties of the device itself and the bulk properties of the fluid (e.g., density, speed of sound in the fluid, viscosity of the fluid).

In any of the foregoing embodiments, the threshold amount for fluctuations or differences which suggest the presence of gas will vary depending on specific properties of the particular resonant sensor system 100, and the sample or control fluids employed. In some embodiments, the threshold amount will be greater than or equal to about $10^{-5}$ parts of the average or expected frequency. In other embodiments, the threshold amount will be between about $10^{-5}$ and about $10^{-6}$ parts of the average or expected frequency. In certain embodiments, the threshold amount is about $1\text{-}2\times10^{-6}$ parts of the average or expected frequency. Similarly, the specified time span for determining an average or baseline frequency will vary with the resonant sensor system, and the sample or control fluids employed. In some embodiments, the time span will be between about 1 second and about 30 minutes, or about 1-5 minutes. In certain embodiments, the time span will be about 2-3 minutes.

Irrespective of any measurements of resonant frequency, the methods of the invention can be practiced automatically or prophylactically with control fluids or sample fluids to reduce the likelihood of gas interference. Thus, even if there are no indications that gas is present in the resonant sensor system, or even if no attempt is made to determine whether gas is present, the methods of the invention can be practiced to reduce the likelihood of gas interference.

Accordingly, the invention in one aspect features a system and method for reducing gas interference. Referring to the embodiment of FIG. 1, a control fluid is contained within reservoir 140. The inlet valve 130 is placed in an open position. Pump 170 is operating thereby causing the control fluid to flow through inlet connector 120 into the fluid chamber 101 and out of the outlet port 150 and through the outlet connector 160. After the control fluid is introduced into the fluid chamber 101, the resonant frequency of the resonant surface is measured for a period of time sufficient to establish a baseline value for the resonant frequency.

The control fluid can be a wetting solution, a fluid having bulk properties substantially similar to the sample fluid, or a fluid, which is identical or substantially similar to the sample fluid but lacks the analyte(s) of interest. If the resonant frequency measured does not fluctuate by more than a threshold amount (e.g., about $10^{-6}$ parts) of the average frequency over a specified time span, and/or the resonant frequency does not differ by more than a threshold amount from an expected frequency, the time average can be used as a baseline. If, however, the resonant frequency does fluctuate more than the threshold amount, and/or the resonant frequency differs from the expected value by more than the threshold amount, gas may be present, and the methods of the invention are practiced to reduce the gas interference. After the gas interference is reduced, a baseline frequency is then established. Alternatively, a sample fluid can be introduced into the resonant sensor system 100 to measure a baseline resonant frequency without previously wetting the fluid chamber 101 with, for example, a control fluid.

In one embodiment, the following steps are taken to reduce the presence of gas in a fluid in the resonant sensor system 100. Initially, inlet valve 130 is open and fluid passes into the fluid chamber 101 due to the pumping action of the pump 170. To reduce the amount of gas in the system 100 (or as a prophylactic measure to reduce the likelihood that gas is actually in the system 100), inlet valve 130 is moved to the closed position to prevent the further flow of control fluid into the fluid chamber 101. Pump 170 is commanded to continue operating with the inlet valve 130 closed, thereby reducing the fluid flow and pressure within the fluid chamber 101. The reduced pressure causes the gas to expand in the fluid chamber 101. The inlet valve 130 is then opened while the pump continues to operate, causing the fluid flow and pressure within the fluid chamber 101 to increase. The increased pressure causes the compression of gas within the fluid chamber 101. Alternating the expansion and contraction of the gas, coupled with the alternating decreased and increased flow rate, disrupts the association of gas with surfaces in the fluid chamber 101, dislodging at least some gas/bubbles and/or reducing at least some unwetted surface area. This process is performed at least once or, alternatively, can be repeated several times to dislodge gas in the system 100, thereby reducing gas interference. Therefore, varying the duration that the inlet valve is in the open configuration can change fluid flow or pressure to, for example, dislodge gas adhered to a surface (e.g., surface of the resonant sensor device) in the fluid chamber.

In some embodiments, gas in the system 100 is reduced by varying the state of the inlet valve between a closed position and an open position in less than about 1 second. In some embodiments, gas is reduced by varying the state of the inlet valve between an open position and a closed position in less than about 0.5 second. By varying the open or closed state of an inlet or outlet valve, for a fluid chamber having a volume of several μls, the change of fluid flow can be about 100-300 microliters per minute for less than about one minute, and a pressure drop between about one and about 3 psi can occur within the fluid chamber.

It should be emphasized that, in a system with a downstream pump 170, either (1) the inlet valve 130 can be operated transiently (e.g., partially or completely opened and closed) while the pump 170 is operating, or (2) the pump 170 can be operated transiently (e.g., by starting and stopping the pump 170 or by varying the speed at which the pump 170 is operated) with the inlet valve 130 closed. Either combination of operating conditions results in a transient reduction of flow rate and pressure and can thereby reduce gas interference by dislodging bubbles or reducing unwetted surface. Conversely, in a system with an upstream pump, either (1) an outlet valve is closed transiently while the pump is operating, or (2) the pump is operated transiently with the outlet valve closed. Either combination will result in a transient increase in flow rate and pressure and thereby reduces gas interference by dislodging bubbles or reducing unwetted surface. In addition, one of ordinary skill in the art would be able to repeat the process as many times as required to remove the gas from the system 100.

In some embodiments, the electronic monitoring device 180 is also connected (directly or indirectly) to other components and devices of the resonant sensor system 100. The electronic monitoring device 180 is capable of controlling the operation of, for example, the pump 170 and the inlet valve 130. In this manner, an operator or an automated controller (not shown) located within the electronic monitoring device 180 can control fluid flow and pressure in the resonant sensor system 100 by altering, for example, the speed of the pump 170 and/or the state (e.g., open, closed, or partially open position) of the inlet valve 130.

In some embodiments, operation of the pump 170 and or inlet valve 130 is controlled based on at least one signal output by the resonant sensor device 100. In some embodiments, the state of the inlet valve is varied by the electronic monitoring device 180 based on at least one signal output by the resonant sensor device 104 until a resonant frequency associated with the at least one signal returns to a predetermined resonant frequency value.

Further, variations on these methods are contemplated in which multiple numbers of input and/or output valves are operated in conjunction with one or more pumps to reduce gas interference and/or reduce the amount of unwetted surface in the resonant sensor system 100. In some embodiments, mechanical or vibratory excitation of a portion of the resonant sensor system 100 (e.g., a housing of the device 104, inlet connector 120) is performed to reduce gas interference in the system 100. By way of example, excitation of the resonant surface 102 by applying a time-varying excitation signal to the device 104 can be used to dislodge gas adhered to the resonant surface 104. Alternatively, an operator can mechanically excite the system 100 by tapping the inlet connector 120 to dislodge gas in the fluid that adheres to an internal surface of the resonant sensor system 100, thereby reducing gas interference.

In some embodiments, fluid pressure can be varied by transiently engaging a pump to induce fluid movement into or out of the fluid chamber. For example, a pump can be engaged for a short period of time (i.e., several seconds) and then be disengaged. Alternatively, or in addition, the rate of fluid flow induced by the pump can also be varied (e.g., increasing the fluid flow rate) to cause transient changes in pressure. Thus, if the pump is initially not operating, it can be transiently operated to effect changes in fluid flow rate and pressure. Alternatively, or in addition, if the pump is already operating, the rate of pumping can be transiently varied to effect changes in fluid flow rate and pressure. In either case, the actual flow rates chosen will depend upon the geometry of the resonant sensor system (e.g., fluid chamber volume, or connector tube and port cross-sectional areas) and the maximum acceptable pressures and shear forces that do not compromise the structures of the system. Maximum acceptable pressures and shear forces for a particular system and sample or control fluids can be determined empirically by one of skill in the art operating the device.

In some embodiments, in order to increase the changes in flow rate and pressure associated with transient operation of a pump, either the inlet valves or the outlet valves are closed during pump operation. Thus, in the case of a pump located downstream of the fluid chamber at the outlet port or along the outlet connector, the inlet valve(s) can be closed during pump operation to effect a greater transient reduction in pressure. In the case of a pump located upstream of the fluid chamber at the inlet port or along the inlet connector, the outlet valve(s) can be closed during pump operation to effect a greater transient increase in pressure. In either case, the valves can be closed prior to transiently operating the pump, or the pump can be continuously operated while the valves are transiently opened and closed. In some embodiments, because a pump may be used to move a control fluid through the resonant sensor system to wet the surfaces (or to produce hydrophilic surfaces, as described below), or to move a sample fluid through the system, it may be more convenient to continuously operate the pump and to use one or more valves to switch between fluid sources and to cause transient changes in fluid flow rate and pressure.

Reduction of Gas Interference by Providing Hydrophilic Surfaces

In order to reduce gas interference in the resonant sensor system 100, surfaces (e.g., the resonant surface 102 or other surfaces in the fluid chamber 101 of FIG. 1) and interfaces can be provided that reduce the likelihood that gas/bubbles will form or localize in the fluid chamber 101, and that reduce the likelihood that surfaces in the fluid chamber 101 will be unwetted or only partially wetted when fluid flows through the fluid chamber 101. These surfaces are described herein as "wettable" surfaces, and are characterized by their wetting properties and the ability of a fluid to coat the surfaces. The wettable surfaces include not only the resonant surface 102, or the areas of the resonant surface 102 which are not occupied by capture agents, but also those interior surfaces of the fluid chamber 101, or of the entire resonant sensor system 100, which are not part of the resonant surface 102. Further, a wettable surface in which a water-based fluid is used in the resonant sensor system 100 is defined as a hydrophilic surface.

Thus, in some embodiments of the invention, the interior surfaces of the fluid chamber, or of the entire resonant sensor system 100, are manufactured from materials which are inherently wettable or which have wettable surfaces or coatings. Examples of such materials include silicon and $O_2$ plasma treated metals.

In other embodiments of the invention, interior surfaces can be treated after manufacturing with buffers or solutions to yield substantially hydrophilic surfaces within the fluid chamber 101 or the entire resonant sensor system 100. For example, surfactants can be utilized to coat hydrophobic surfaces and produce a relatively hydrophilic surface. Non-limiting examples of surfactants used to increase the hydrophilic character of a surface are Tergitol, NP40, Triton X-100, Tween® 20, Tween® 40, Tween® 65, TWEEN® 80, Tween® 85, 3-[(3-Cholamidopropyl) dimethylammonio]-1-propanesulfonate, 2,4,7,9-Tetramethyl-5-decyne-4,7-diol ethoxylate, MERPOL® OJ, MERPOL® SE, and MERPOL® SH. Alternatively, amphipathic proteins, such as albumins (e.g., ovalbumin, serum albumin), oleosins, gelatin and casein can be employed. Alternatively, polymeric hydrocarbons containing hydrophilic domains can be used to coat surfaces and reduce water tension. Non-limiting examples of such polymeric hydrocarbons are polyethylene glycol, poly(ethylene glycol) methyl ether, ethylene glycol monosalicylate, di(ethylene-d8-glycol), di(ethylene glycol) 2-ethylhexyl ether, di(ethylene glycol) benzyl ether, di(ethylene glycol-d2), and di(ethylene glycol) hexyl ether. In the case of polyethylene glycol (PEG), polymers of varying numbers of repeating units of PEG can be employed without altering the coating characteristics of the compound, provided that the PEG does not disrupt the resonant sensor function through steric hindrance.

In some embodiments, interior surfaces of the resonant sensor system 100 (e.g., the resonant surface 102, other surfaces in the fluid chamber 101, the interior surfaces of the inlet connector 120 and the outlet connector 160 of FIG. 1) are exposed to solutions or control fluids that include Stabil-Coat® biomolecule stabilizer or StabilGuard® immunoassay stabilizer both sold by SurModics, Inc. (Eden Prairie, Minn.). StabilCoat aids in providing hydrophilic surfaces in the system 100 in addition to preserving the conformation and activity of dried proteins (e.g. antibodies, antigens) in immunoassays. StabilGuard aids in providing hydrophilic surfaces in the system 100 in addition to preserving the conformation and activity of dried proteins (e.g. antibodies, antigens) in immunoassays, without the use of bovine protein.

In some embodiments, control fluids containing surfactants, amphipathic proteins, or polymeric hydrocarbons can be flowed through the system 100 immediately prior to the introduction of the sample fluid. Alternatively, the sample fluid can contain such surfactants, amphipathic proteins, or polymeric hydrocarbons, and these compounds can be applied as the sample fluid is being tested. Hydrophilic surface-forming compounds can be dissolved in solutions including, but not limited to, phosphate buffered saline (PBS), Tris buffered saline (TBS), Tris base, and sodium chloride, sodium citrate buffer (SSC). These solutions can be included in control fluids or sample fluids.

In other embodiments, hydrophilic surface-forming compounds can be applied to the surfaces (e.g., interior surfaces of tubes or connectors 120 and 160, the resonant surface 102) of the resonant sensor system 100 substantially prior to the testing of a sample fluid (e.g., hours, days, weeks, months before). In such cases, the hydrophilic surface-forming compound is allowed to adhere to the surfaces for an indefinite period of time while retaining the ability to form a hydrophilic surface. In some embodiments, a separate reservoir for such hydrophilic surface-forming solutions can be provided.

Resonant Sensor Device Configurations

In addition to the resonant sensor device 104 described in FIG. 2, alternative types of resonant sensor devices are contemplated that can be produced in a variety of other configurations, known in the art, in which resonant movement is imparted to variously shaped and constructed resonant surfaces by various forms of actuators. Each of these contemplated devices can be used to detect properties of a fluid in contact with the resonant surface 102 of the resonant sensor device 104 and/or detect the presence and quantity of an analyte in a fluid in contact with the resonant surface 102 of the resonant sensor device 104.

Referring to FIG. 2, the membrane 234 of the device 104 can, for example, be composed of materials including, but not limited to, silicon, silicon nitride, silicon dioxide, oxy-nitride, aluminum nitride, and diamond. In some embodiments, the thickness of the thin film membrane can be between about 1.5 µm and about 2.5 µm, between about 1.7 µm and about 2.3 µm, and between about 1.9 µm and about 2.1 µm. Non-limiting examples of piezoelectric materials used to produce a piezoelectric layer 236 include quartz (SiO2), barium titanate (BaTiO3), and aluminum nitride. Other materials that produce an electric field when the material changes dimensions as a result of an imposed mechanical force can be used as the layer 236 of the device 104. The thicknesses of the piezoelectric layer 236 can vary, for example, from about 0.1 µm to about 1.0 µm, from about 0.2 µm to about 0.9 µm, from about 0.3 µm to about 0.8 µm, from about 0.4 µm to about 0.7 µm, or from about 0.5 µm to about 0.6 µm.

Capture agents specific for a particular analyte can be placed onto the resonant surface 102. In some embodiments, the capture agents can be associated with a gold-coated resonant surface 102 through self-assembled monolayers composed of thiol-terminated alkyl chains. Capture agents can be associated with the resonant surface 102 through other means known in the art and described below. In addition, the membrane 234 can be coated with a metal layer 240 (e.g., gold) to allow for improved self-assembled monolayer association with the membrane 234. The exposed surface (e.g., layer 234) of the device 104 is rendered substantially hydrophilic using materials including, but not limited to, surfactants, polymeric hydrocarbons, or amphipathic proteins.

Referring to FIG. 1, in another embodiment, the resonant sensor device 104 is a quartz crystal microbalance ("QCM") device disposed in the fluid chamber 101. An oscillator circuit creates an operating frequency through the surface of the QCM device. The oscillator circuit generates an alternating potential across the surface through electrodes connected to opposite points on the surface. The alternating current causes vibrations in the surface, which generates a frequency. The frequency range across the surface can, for example, be between about 1 MHz and about 30 MHz, between about 5 MHz and about 25 MHz, between about 10 MHz and about 20 MHz, and between about 12 MHz and about 18 MHz.

The surface of the QCM device is comprised of quartz. The surface can be coated with various substances including, but not limited to, gold and aluminum. Coatings that increase the thickness of the surface also increase the sensitivity of the resonant sensor device 104 to added mass associated with analyte binding.

Referring to FIG. 1, in some embodiments, the resonant sensor device 104 is a surface acoustic wave ("SAW") device. In these embodiments, the resonant surface 102 is composed of non-limiting substances such as quartz or GaAs. The resonant surface 102 has two interdigital transducers or electrodes placed on opposing sides of the resonant surface 102. The device 104 has an actuator that is an input transducer that causes a displacement in the resonant surface 102 that propagates away from the transducer like a "wave." The wave reaches an output transducer of the device 104 that transmits the wave to a device or system (e.g., the electronic monitoring device 180 of FIG. 1) that detects an electrical signal corresponding to at least one property (e.g., frequency, amplitude, and/or phase) of the wave. The frequency of the wave can be modulated by an electrical signal applied to the actuator or by changes in the mass on the resonant surface 102 of the device 104. Changes in mass occur when, for example, analytes in a sample become bound to capture agents disposed on the resonant surface 102 of the SAW device. Methods of producing SAW devices are known in the art and have been described previously (see, e.g., Josse et al. (2001) *Anal. Chem.* 73(24): 5937-5944).

Furthermore, in other embodiments, the resonant sensor device 104 is a Thickness Shear Mode Resonator ("TSM") device. These embodiments comprise a thin disk of AT-cut quartz (angle of the plate in the quartz crystal that supports a shear deformation and a zero first-order temperature coefficient), with metal (e.g., gold over chromium) electrodes deposited on each face. Application of a potential (voltage) to the electrodes produces a large electric field through the bulk of the quartz. The electric field produces a strain or displacement in the quartz. By oscillating the frequency, a mechanical resonance is created and the mechanical wave moves across the quartz surface. In one embodiment, capture agents are bound to the resonant surface 102 of the TSM device. As analytes bind to the capture agents, the frequency and amplitude of the wave moving across the resonant surface 102 changes in accordance with the increased mass associated with the capture agents located on the resonant surface 102 of the device 104. Alternatively, the TSM device can be used to measure the bulk fluid properties of a fluid sample. These embodiments would not require the addition of capture agents to the resonant surface 102 of the TSM device.

Capture Agents and Linkages

The capture agents employed in a specific embodiment of the invention depend on the nature of the analyte to be detected using a resonant sensor system (e.g., the resonant sensor system 100 of FIG. 1). Non-limiting examples of capture agents include antibodies, polynucleotides, aptamers, cell surface receptors, cytoplasmic receptors, binding domains, small molecule ligands, sugars, polysaccharides, glycans, glycoproteins and other compounds known to those of skill in the art.

In particular, antibodies can be used as capture agents in the resonant sensor devices of the invention. As used herein, the term "antibody" is intended to include naturally produced antibodies, recombinantly produced antibodies, monoclonal antibodies, and polyclonal antibodies, as well as antibody fragments such as Fab fragments, F(ab')$_2$ fragments, Fv fragments, and single-chain Fv (scFv) fragments. Useful antibody receptors include all immunoglobulin classes, such as IgM, IgG, IgD, IgE, IgA and their subclasses. Antibodies may be produced by standard methods, well known in the art (see, e.g., Pluckthun (1990), *Nature* 347:497-498; Huse et al. (1989), *Science* 246:1275-1289; Chaudhary et al. (1990), *Proc. Natl. Acad. Sci. USA* 87:1066-1070; Mullinax et al. (1990), *Proc. Natl. Acad. Sci. USA* 87:8095-8099; Berg et al. (1991), *Proc. Natl. Acad. Sci. USA* 88:4723-4727; Wood et al. (1990), *J. Immunol.* 145:3011-3016).

Alternatively, capture agents can be polynucleotides bound to the resonant sensor surface 102. As used herein, the term "polynucleotide" includes any molecule comprising a sequence of covalently joined nucleoside-like chemical units that has selective binding affinity for a nucleic acid of complementary or substantially complementary sequence under appropriate conditions (e.g., pH, temperature, solvent, ionic strength, electric field strength). Polynucleotides include naturally occurring nucleic acids such as DNA or RNA, as well as nucleic acid analogues with modified nucleosides or internucleoside linkages, and molecules which have been modified with linkers or detectable labels, which facilitate immobilization on a substrate or which facilitate detection. Modifications to internucleoside linkages include, but are not limited to, those linkages that provide other chemical groups that incorporate additional charge, polarizability, hydrophobicity, hydrogen bonding, or electrostatic interaction.

Other capture agents envisioned by the present invention include cell surface receptors (e.g., immune system molecules such as MHC antigens, T cell receptors and CD antigens, protein and peptide hormone receptors such as the thyroid-stimulating hormone, luteinizing hormone, follicle-stimulating hormone, calcitonin, somatotropin, vasopressin, parathyroid hormone, insulin and glucagon receptors; catecholamine receptors such as the dopamine, epinephrine and norepinephrine receptors; eicosanoid receptors such as the prostaglandin receptors; folic acid receptors), cytoplasmic receptors (e.g., thyroid hormone receptor, peroxisome proliferator-activator receptors (PPARs), and steroid receptors such as the estrogen, androgen, mineralocortocoid and glucocorticoid receptors), binding domains (e.g., DNA, RNA, metal, glycosaminoglycan, ubiquitin, cofactor and other ligand binding domains of various proteins), small molecule ligands (e.g., nucleotide mono-, di- and triphosphates, members of combinatorial chemistry libraries, members of peptide libraries), sugars (e.g., lactose, trehalose, L-arabinose, D-maltose), polysaccharides (e.g., bacterial endotoxin, mannan, pullulan, amylopectin, dextran), glycans (e.g., glycosaminoglycans (GAGs), glycosylation structures), and glycoproteins (e.g., lectins).

In some embodiments, capture agents are adsorbent, thin polymer layers that bind an analyte. Chemo-selective polymers have been developed previously and are known to the art (see, e.g., McGill et al., (1994) *Choosing Polymer Coatings for Chemical Sensors, Chemtech.* 24(9): 27-37; Houser et al., (2001) *Talanta* 54:469-485). Such adsorbent polymeric layers can range in thicknesses, for example, between about 10 nm and about 1 µm, between about 100 nm and about 900 nm, between about 200 nm and about 800 nm, or between about 250 nm and about 750 nm.

In some embodiments, capture agents can be bound to the resonant surface directly through covalent or non-covalent bonds. For example, polymeric hydrocarbon surfaces (e.g., polystyrene surfaces) can be treated with an acid to create reactive groups to which capture agents can covalently bind. As another example, capture agents such as nucleic acids and proteins can bind to nylon and PVDF membranes through non-covalent bonds such as hydrophilic interactions.

In addition to direct association of capture agents with a resonant surface, resonant surfaces can be chemically altered or derivatized to produce reactive groups to which capture agents can be bound. For example, a gold surface of a resonant surface can be treated with thiocyctic acid, which creates thiol groups directly bound to the gold surface (see, e.g., Lyle et al. (2002), *Analyst* 127(12): 1596-1600), to which capture agents can subsequently be bound by reaction with the thiol groups. As another example, polystyrene surfaces can be vacuum-gas plasma treated to add a layer of negatively charged reactive groups to the resonant surface. The negatively charged groups are then used for covalently binding capture agents.

In some embodiments, bifunctional organic chains (i.e., organic chains with at least two reactive groups) are used to bind capture agents to a resonant surface. The reactive group of the organic chain which is bound to the resonant surface is designated the "alpha" group and the reactive group of the organic chain which is bound to the capture agent is designated the "omega" group. The particular reactive groups which are employed in the organic chains will depend upon the nature of the available reactive groups on the resonant surface and the capture agent. Non-limiting examples of potentially useful reactive groups for organic chains include ethers, alcohols, thiols, glycols, esters, carboxyls, carbonyls, amides, and amines located at or near an end of the organic chain.

In other embodiments, capture agents can be bound to the resonant surface using specialized organic chains which form self-assembled monolayers (SAMs). SAM-forming molecules have alpha groups suitable for binding to a resonant surface and omega groups suitable for binding to a capture agent as described above. In addition, SAM-forming molecules include central hydrophobic organic chains of varying lengths between the alpha and omega groups that cause association of SAM-forming molecules through hydrophobic associations. As a result of the association of the central hydrophobic organic chains, neighboring molecules form a SAM in which the SAM-forming molecules are disposed in a packed arrayed of substantially parallel molecules. The omega groups which terminate one end of the SAM-forming molecules are disposed on the surface of the SAM distal from the resonant surface and are available for binding to capture agents.

In some embodiments, the central portion of the molecules comprising the SAM-forming molecules can include a spacer functionality connecting the alpha reactive group and the omega reactive group. Alternatively, the spacer may essentially comprise the omega group, if no particular reactive group is required (e.g., for blocking molecules). Any spacer that does not disrupt SAM packing and that allows the SAM layer to be somewhat impermeable to organic or aqueous environments is suitable. The spacer may be polar, non-polar, halogenated (e.g., fluorinated), positively charged, negatively charged, or uncharged. For example, a saturated or unsaturated, linear or branched alkyl, aryl, or other hydrocarbon spacer may be used.

SAMs can be applied to surfaces by a variety of techniques well known in the art, including simple flooding of a surface to produce an even layer, or more sophisticated methods such as microstamping and irradiative patterning to produce predetermined patterns on the resonant surface.

The resonant surface of a resonant sensor device (e.g., the resonant sensor device 104 of FIG. 1) can comprise a compound or composition that allows SAMs and/or capture agent molecules to associate with the resonant surface. Non-limiting examples of such compounds or compositions are carbon (e.g., graphite), glasses, plastics, polypropylene, polystyrene, doped polystyrene, polycarbonate, PTFE, ULTEM®, PET, polyvinylidene fluoride (PVDF), polysilicon, silicon, silicon carbide, silicon dioxide, and silicon nitride. In addition, the surface can consist of metals such as gold, aluminum, aluminum nitride, aluminum oxide, gallium arsenide, cadmium, chromium, copper, molybdenum, molybdenum silicide, nickel, palladium, phosphor bronze metal, platinum, silver, stainless steel, tantalum, tellurium, thallium, tin, titanium, titanium aluminum, titanium boride, titanium carbide, titanium nickel, titanium nitride, titanium oxide, tungsten, tungsten carbide, tungsten silicide, zinc, zinc oxide, zircon, and zirconium oxide.

The surface can also be coated with a variety of compounds to improve the capacity of the surface to bind capture agents, organic chains or SAMs. Non-limiting examples of such coatings are gold, tungsten, gallium arsenide, zircon, zirconium oxide, titanium, titanium aluminum, titanium carbide, titanium nitride, titanium oxide, sodium silicate, silicon nitride, silicon oxide, silicon dioxide, silicon carbide, platinum, aluminum, aluminum oxide, nitride coatings, niobium oxide, molybdenum silicide, molybdenum, and zinc oxide. Metallic coatings can be coated onto surfaces at thicknesses of between about 10 and about 10,000 Angstroms. Methods of deposition include, but are not limited to, evaporation, sputtering, and electroplating.

Figure 4:
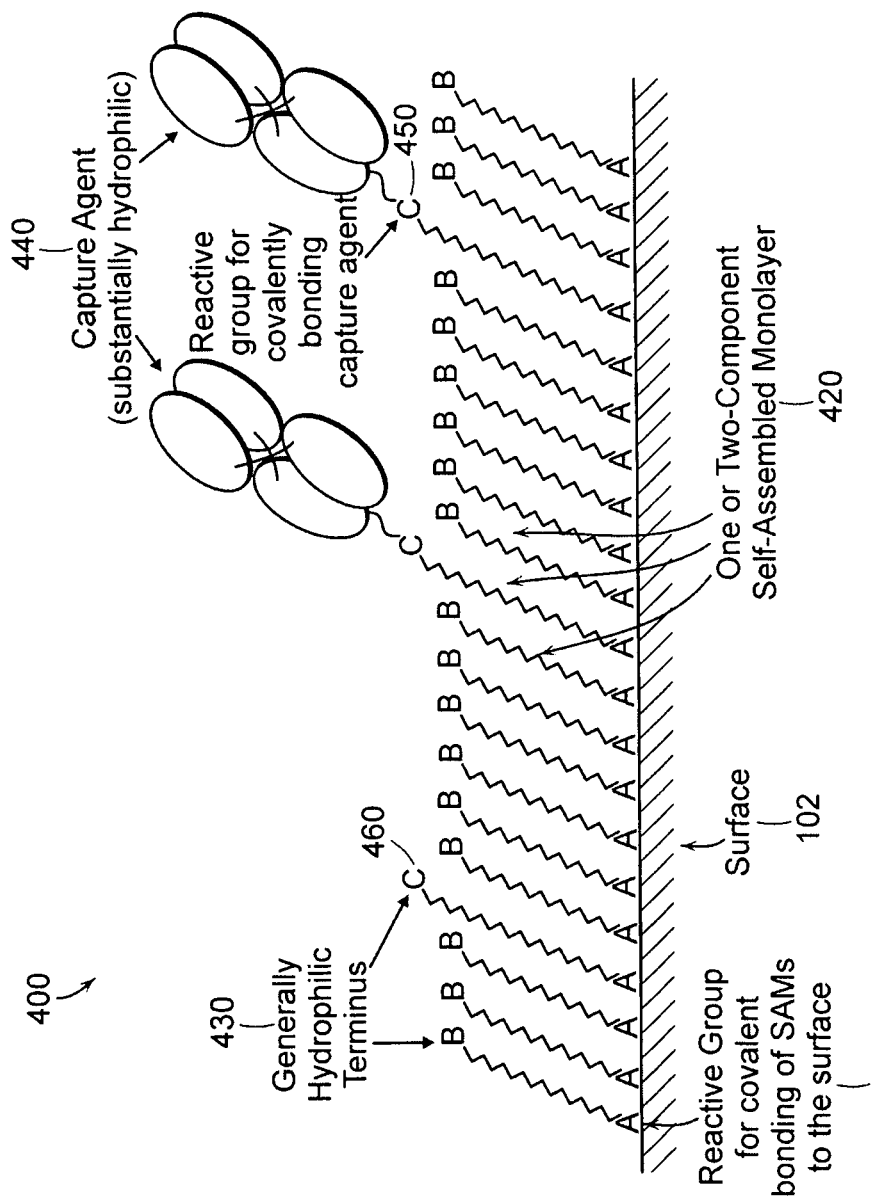
FIG. 4 is a schematic view of substances associated with a fluid surface of a resonant sensor system, according to one embodiment of the invention.

By way of example, FIG. 4 illustrates a schematic view 400 of substances associated with a surface (e.g., the resonant surface 102 of FIG. 1) of a resonant sensor system. In this embodiment, the substances make the surface 102 of a resonant sensor device 104 substantially hydrophobic. The surface 102 has a metal layer (e.g., gold) disposed on the surface 102. A reactive group 410 is applied to the surface 102. Self-Assembled Monolayers (SAMs) 420 are covalently bonded to the reactive group 410. The SAMs 420 can be, for example, one or two-component SAMs.

A generally hydrophobic terminus 430 is located at an end 460 of at least some of the SAMs 420. At least some of the ends 460 of the SAMs instead have a reactive group 450. A substantially hydrophilic capture agent 440 is bound to the reactive groups 450. In this manner, a resonant sensor surface 102 of a resonant sensor device has a substantially hydrophilic surface due to the binding of the hydrophilic terminus 430 and the hydrophilic capture agents 440. The hydrophilic surface reduces the likelihood that gas will adhere to the surface 102 to interfere with measurements made to, for example, detect the presence of an analyte that a fluid would supply to the system to be bound to the capture agents 440.

Pumps, Valves and Connectors

As described herein, reduction of gas interference can be accomplished by use of wettable surfaces in a resonant sensor system and/or by varying the fluid flow and pressure in the fluid chamber of a resonant sensor device. A pump disposed upstream of the fluid chamber causes increased fluid pressure as the pump increases the fluid flow rate into the fluid chamber. Conversely, a pump disposed downstream of the fluid chamber causes decreased fluid pressure as the pump increases the fluid flow rate out of the fluid chamber. Because increases in pressure may cause leaks of potentially hazardous sample fluids from damaged joints, seals and other structures in the resonant sensor system, it may be preferred to use downstream pumps in certain embodiments where such leakage is of concern.

A variety of pumps can be used in the present invention to move fluid through the fluid chamber. Pumps can produce fluid flow by externally compressing or sequentially constricting a segment of a fluid channel (e.g., a compressible connector or tube). Non-limiting examples of such pumps include peristaltic pumps. Alternatively, a pump can produce fluid flow by impelling fluid that has entered an internal chamber of the pump. For example, centrifugal pumps and rotary pumps induce fluid flow by pushing the fluid with an impeller or rotor disposed in an interior chamber of the pump. Also, electro-osmotic pumps can be used to move fluid using an electric field to move ions in the fluid, thereby generating fluid movement (see, e.g., Jiang et al. (2002), *Proc. Therm. Chal. Next Gen. Elec. Sys., THERMES*, Santa Fe, N. Mex., January 13-16, pp. 133-139

Valves useful in the invention include any manner of valve which can function with the selected inlet or outlet ports or connectors to control fluid flow entering or exiting the fluid chamber. Such valves include external valves that exert pressure on a compliant fluid channel to prevent fluid flow, or internal valves that prevent fluid flow by providing a barrier to fluid flow that is internally disposed within the fluid channel.

Non-limiting examples of external valves are clamps, clips, push-in valves, compression valves, diaphragm valves, and Skinner valves. Generally, external valves can utilize a bar or other solid device to compress a tube and prevent fluid flow.

Non-limiting examples of internal valves are stopcock valves and faucet-valves that prevent fluid flow by allowing an operator to switch between an open position and a closed position by using a handle disposed on the valve. Stopcock valves can be obtained commercially from, for example, Saint-Gobain Performance Plastics Microelectronics (Garden Grove, Calif.).

In some embodiments, valves are operated manually and, in other embodiments, valves are operated automatically or remotely using electronic control systems or devices. In some embodiments, the valves are closed and opened in about 1 to 2 seconds. In some embodiments, the valves can be opened or closed within about 0.5 seconds.

Connectors employed in the present invention can be channels defined in solid structures (e.g., channels in blocks of material), tubes which connect different structures (e.g., plastic tubing between reservoirs and chambers), or any other means of providing fluid communication between reservoirs and chambers. In some embodiments, the inlet and/or outlet connectors are tubing comprised of plastic, polyethylene, nylon, stainless steel, brass, and copper. In particular, flexible plastic tubing (e.g., Tygon® tubing; Carolina Biological Supply Company, Burlington, N.C.) can be used with external pumps or valves.

The following examples illustrate some preferred modes of practicing the present invention, but are not intended to limit the scope of the claimed invention. Alternative materials and methods may be utilized to obtain similar results.

Examples

In one embodiment, the resonant sensor system 100 of FIG. 1 is produced with the resonant sensor device 104 of FIG. 2. The resonant sensor device 104 is a flexural plate wave device. The device is produced from a silicon wafer using microfabrication techniques. A cavity is etched into the silicon wafer to produce a suspended membrane (234) that is approximately 1.6 mm long and 0.4 mm wide. The cavity depth 232 is approximately the wafer thickness, which in this case is 0.5 mm. The membrane 243 is a composite layer consisting of 2 µm of silicon (Si) with 0.5 µm of a piezoelectric aluminum nitride (AlN) (layer 236). Two sets of interdigitated metal electrodes 238 are deposited on top of the AlN layer 236. A time-varying electrical signal is applied to one set of electrodes to generate vibrations in the structure. The vibration characteristics of the resonant device 104 are monitored using the second set of electrodes 238. When a liquid, such as water, is in contact with one side of the structure, the pass band response of the plate structure is between about 15 to about 25 MHz (reference signal). An electronic monitoring device 180 compares the reference signal to the sensor signal to determine the changes (e.g., due to analyte bound to the resonant surface 102 of the resonant sensor device 104) in the relative magnitude and phase angle as a function of frequency. From this information, the presence of differing fluids and relative mass, viscous and acoustic analyte loading of the sensor surface is detected.

The resonant device 104 is packaged such that a fluid sample contacts the device 104 on the side opposite to that of the electrodes on the piezoelectric material, in the cavity 232. A gold layer 240 (between ~500-5000 Å) is deposited on the resonant surface 102 of the resonant sensor device 104. Thiol-terminated alkyl chains are linked to the gold surface 104 forming a substantially hydrophilic self-assembled monolayer (SAM). A fraction of the SAM chains are terminated with reactive groups, such as carboxyl, to allow covalent linking of capture agents using standard biochemical process steps. Capture agents particular to the analyte in the fluid are applied. The remainder of the SAM chains are terminated with non-reactive groups that have a hydrophilic character and, therefore, resist gas interference (e.g., PEG). The resonant sensor device 104 is used to detect and quantify the presence of the analyte in the fluid.

The resonant sensor device 104 is packaged in a customized manifold 242 that defines an inlet port 110 and an outlet port 150 and a fluid chamber 101. Fluids are directed through the inlet port 110 by a manifold or body 242 component that interfaces with standard medical grade tubing (e.g., PharMed & Tygon). Manifold or body 242 materials used include metals such as aluminum or inert stainless steel (e.g., SS 316) and plastics that can be rendered inert, such as Teflon, polycarbonate or polyethylene. Fluid passages 215 are drilled, and/or machined, and/or formed via standard molding practices. The fluid chamber 101 within the manifold 242 defines a volume of approximately several µls. Manifold (242) and tubing/connectors 120 attached to the resonant sensor device 104 defines fluid volumes of between about 10 µl to about 100 µl (depending upon design considerations for a specific embodiment).

Prior to use, the packaged resonant sensor systems 100 are wetted with a nonionic surfactant for about 1-30 minutes. In one embodiment, a standard 1x (10 mM) phosphate buffered saline with 0.05% Tween-20 (Sigma Chemicals, St. Louis, Mo.) is used to wet the surfaces of the resonant sensor system. Wetting coats the hydrophobic parts of the package internal surfaces with the surfactant. During this period a combination of techniques (similar to those described previously herein) are used to dislodge gas from within the vicinity of the resonant surface 102.

Inlet tubing (PharMed & Tygon) carries a sample fluid to the manifold 242 and subsequently into the fluid chamber 101. In some embodiments, the tubing branches to allow two or more fluids enter the fluid chamber 101 (for example, as described in FIG. 3). A pinch valve 120 (Instech PV256, ChemValve, Instech Laboratories, Inc. Plymouth Meeting, Pa.) regulates which tube passage (120a or 120b) is initially open. A peristaltic pump 170 (Instech Laboratories, Inc. Plymouth Meeting, Pa.) draws fluid through the fluid chamber 101 and pumps it into a waste reservoir 116. Typical flows vary between about 10 µl/min to 200 µl/min. In one embodiment, an additional valve (not shown) located at the inlet 110 is then commanded to be fully closed, pinching off all flows to the fluid chamber 101. The pump 170 continues to draw, decreasing the pressure in the fluid in the fluid chamber 101. Pressures as low as several pounds per square inch below atmospheric pressure are typically generated. After approximately 0.1-10.0 seconds, the additional valve is opened and a pressure and flow pulse results. Gas pockets and bubbles in the resonant sensor system 100 (e.g., the fluid chamber 101) that are lodged in the vicinity of the resonant surface 102 are dislodged and carried downstream by the flows.

In other embodiments, valves are instead placed at the outlet 150 of the fluid chamber 101, at a location upstream of the peristaltic pump. In this situation, closing the valve while pumping serves to lower the pressure in the section of tubing between the pump and the valve. Upon releasing the valve the subsequent flow surging is sufficient to dislodge gas that resides within the vicinity of the resonant surface 102.

During the wetting period an operator can, for example, examine the signals associated with the resonant sensor device. When gas is present in the fluid in the fluid chamber or a portion of the resonant sensor system the signals are highly sensitive and exhibit oscillations and jumps that are 100's and 1000's of parts per million of the resonance frequency. Gas interference can be assessed by observing the change in signals associated with the resonant sensor device as flow speeds are varied and/or before and after flow and pressure transients are generated (as described herein) that dislodge and clear out gas. The methods of reducing gas interference can be repeated until a sufficient level of signal stability is achieved (e.g., the resonant frequency does not vary over a period of several seconds by more than about 1-10 parts per million of resonance frequency.

In another embodiment, gravity is used to draw fluid from a supply from one or more sample vials (reservoirs) through the fluid chamber and to waste vials (reservoirs). In this case impacting, or flicking, tube attached to an outlet of the fluid chamber can be sufficient to dislodge some of the trapped gas within the fluid chamber.

Further, for applications involving measurement of biological analytes in a fluid sample, surfaces of the resonant sensor device are wetted with 1× phosphate buffered saline with 0.05% Tween 20. The sensor packaging is pretreated with some or all of the following: nonionic detergents (NP40, Tween 20, TritonX100), protein blockers (Bovine Serum Albumin (BSA), goat serum, Human Serum Albumin, Blockit), and PolyEthylene Glycol (PEG). In one example regarding detecting biological analytes, stable resonant sensor signals of about 1-10 ppm resolution has been achieved.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize, or be able to ascertain using no more than routine experimentation, many equivalents to the specific embodiments of the invention described specifically herein. Such equivalents are intended to be encompassed in the scope of the appended claims.

What is claimed is:

1. A method of reducing interference from gas in a resonant sensor system, the method comprising:
   (1) providing a resonant sensor system comprising:
       (a) a fluid chamber defined by a plurality of interior surfaces;
       (b) a resonant sensor device defining at least one interior surface of said fluid chamber or disposed within said fluid chamber;
       (c) at least one inlet port and at least one outlet port in fluid communication with said fluid chamber;
       (d) an inlet valve adapted to selectively allow a fluid flow through the at least one inlet port; and
       (e) a pump disposed downstream of the fluid chamber in fluid communication with the at least one outlet port, the pump adapted to pump a fluid through the fluid chamber;
   (2) opening the inlet valve and permitting the fluid to flow through the fluid chamber using the pump;

closing the inlet valve while continuing to use the pump to generate a decrease in fluid pressure within the fluid chamber; and re-opening the inlet valve while continuing to use the pump to permit the fluid to resume flowing through the fluid chamber and to increase fluid pressure within the fluid chamber, the re-opening the inlet valve and the increase in fluid flow and fluid pressure within the fluid chamber reducing interference from gas in the fluid by at least one of: (i) dislodging bubbles from the fluid chamber or (ii) reducing unwetted surface of the resonant sensor device.

2. The method as in claim 1, wherein opening said inlet valve comprises moving said inlet valve from a closed position to an open position in less than about 1 second.

3. The method as in claim 1, wherein opening said inlet valve comprises moving said inlet valve from an open position to a closed position in less than about 0.5 seconds.

4. The method as in claim 1, wherein the fluid comprises a surfactant fluid to increase wettability of at least one of said plurality of interior surfaces prior to flowing a sample fluid through said fluid chamber.

5. The method of claim 1, further comprising monitoring a signal output by the resonant sensor device.

6. The method as in claim 5 wherein said step of monitoring comprises:
 (a) determining a resonant frequency associated with said signal during a period of varied flow of a uniform fluid sample through said fluid chamber;
 (b) detecting changes in resonant frequency greater than about 20 parts per million during said period of varied flow of said uniform fluid sample.

7. The method as in claim 6 wherein said period is between about 1 and about 2 seconds.

8. The method as in claim 6 wherein said period is less than about 1 second.

9. The method as in claim 6, wherein the fluid comprises a surfactant to increase wettability of at least one of said plurality of said interior surfaces prior to flowing a sample fluid through said fluid chamber.

10. The method as in claim 9 wherein said surfactant fluid comprises a composition selected from the group consisting of Tergitol, NP40, Triton X-100, TWEEN 20 (polysorbate 20), TWEEN 40 (polysorbate 40), TWEEN 65 (polysorbate 65), TWEEN 80 (polysorbate 80), TWEEN 85 (polysorbate 85), 3-[(3-Cholamidopropyl)dimethylammonio]-1-propanesulfonate, 2,4,7,9-Tetramethyl-5-decyne-4,7-diol ethoxylate, MERPOL OJ (alcohol ethoxylate), MERPOL SE (alcohol ethoxylate), and MERPOL SH (alcohol ethoxylate).

11. The method of claim 5, wherein said signal indicates the presence of the gas in the fluid.

12. The method of claim 5, comprising repeating the steps of closing and re-opening the inlet valve and monitoring the signal until a resonance associated with the signal returns to predetermined resonance value.

13. The method of claim 12, wherein the predetermined resonance value is no more than 10 parts per million.

14. The method of claim 12, wherein the predetermined resonance value is no more than 1 to 10 parts per million.

15. The method of claim 5, wherein the closing and re-opening said inlet valve is based on the signal output by the resonant sensor device.

16. The method of claim 15 further comprising repeating the steps of closing and re-opening the inlet valve and monitoring the signal until reduction of gas interference is detected.

17. The method of claim 5, further comprising varying the fluid flow during the step of monitoring.

18. The method of claim 17, wherein varying the fluid flow during the step of monitoring comprises changing said at least one of the flow rate or pressure within the fluid chamber based on whether a value associated with the resonant frequency varies by more than a pre-determined amount.

19. The method of claim 18, wherein said pre-determined amount is between about 100 parts per million and about 1000 parts per million.

20. The method of claim 1, wherein the opening, closing, and re-opening the inlet valve is completed within 0.1-10 seconds.

21. A method of reducing interference from gas in a resonant sensor system, the method comprising:
 (1) providing a resonant sensor system comprising:
  (a) a fluid chamber defined by a plurality of interior surfaces;
  (b) a resonant sensor device defining at least one interior surface of said fluid chamber or disposed within said fluid chamber;
  (c) at least one inlet port and at least one outlet port in fluid communication with said fluid chamber;
  (d) an inlet valve adapted to allow a fluid flow into said fluid chamber through said inlet port when said inlet valve is in an open position, and to prevent said fluid flow into said fluid chamber through said inlet port when said inlet valve is in a closed position;
  (e) a first pump disposed downstream of the fluid chamber in fluid communication with the at least one outlet port, the pump adapted to pump a fluid from said fluid chamber through said outlet port; and
  (f) electronic monitoring means for detecting a signal from said resonant sensor device;
 (2) monitoring said signal to detect the presence of said gas in said fluid in said fluid chamber;
 (3) opening the inlet valve and permitting the fluid to flow through the fluid chamber using the pump;
  closing the inlet valve while continuing to use the pump to generate a decrease in fluid pressure within the fluid chamber; and
 re-opening the inlet valve while continuing to use the pump to permit the fluid to resume flowing through the fluid chamber and to increase fluid pressure within the fluid chamber, the re-opening the inlet valve and the increase in fluid flow and fluid pressure within the fluid chamber reducing interference associated with the gas in the fluid by at least one of: (i) dislodging bubbles from the fluid chamber or (ii) reducing unwetted surface of the resonant sensor device; and
 (4) repeating steps (2) and (3) until said gas is not detected.

22. The method as in claim 21, wherein said step of monitoring comprises:
 (a) observing a frequency associated with said signal during a period of consistent flow of a uniform fluid sample through said fluid chamber;
 (b) detecting changes in said frequency greater than about 20 parts per million during said period of consistent flow of said uniform fluid sample.

23. The method as in claim 22, wherein said period is between about 1 second and about 2 seconds.

24. The method as in claim 22, wherein said period is less than about 1 second.

25. The method of claim 21, wherein the opening, closing, and re-opening the inlet valve is completed within 0.1-10 seconds.

* * * * *